United States Patent
Furness, III et al.

(10) Patent No.: US 10,299,735 B2
(45) Date of Patent: May 28, 2019

(54) AUTOMATED DIAGNOSIS BASED AT LEAST IN PART ON PULSE WAVEFORMS

(71) Applicant: PULSE TECTONICS LLC, Seattle, WA (US)

(72) Inventors: Thomas Adrian Furness, III, Seattle, WA (US); Ross Melville, Everett, WA (US); Robert Doane, Bainbridge Island, WA (US); Brian Pal, Medina, WA (US)

(*) Notice: Subject to any disclaimer, the term of this patent is extended or adjusted under 35 U.S.C. 154(b) by 270 days.

(21) Appl. No.: 15/505,844

(22) PCT Filed: Aug. 21, 2015

(86) PCT No.: PCT/US2015/046386
§ 371 (c)(1),
(2) Date: Feb. 22, 2017

(87) PCT Pub. No.: WO2016/029166
PCT Pub. Date: Feb. 25, 2016

(65) Prior Publication Data
US 2017/0258336 A1 Sep. 14, 2017

Related U.S. Application Data

(60) Provisional application No. 62/040,990, filed on Aug. 22, 2014.

(51) Int. Cl.
*A61B 5/024* (2006.01)
*A61B 5/026* (2006.01)
(Continued)

(52) U.S. Cl.
CPC ............ *A61B 5/7246* (2013.01); *A61B 5/024* (2013.01); *A61B 5/026* (2013.01); *A61B 5/0402* (2013.01);
(Continued)

(58) Field of Classification Search
CPC ................................ A61B 5/024; A61B 5/026
See application file for complete search history.

(56) References Cited

U.S. PATENT DOCUMENTS 5,511,546 A     4/1996   Hon
6,135,966 A * 10/2000   Ko ......................... A61B 5/024
                                                                128/925

(Continued)

OTHER PUBLICATIONS

International Search Report, dated Nov. 30, 2015, for PCT/US2015/046386, 4 pages.

(Continued)

*Primary Examiner* — John R Downey
(74) *Attorney, Agent, or Firm* — Seed IP Law Group LLP

(57) ABSTRACT

A front-end system collects diagnostically relevant information or data, including pulse waveform information, and optionally timing information, symptom information, and/or diagnostic information. One or more sensors or transducers detect pulse waveforms in a consistent manner, across various subjects and practitioners. A back-end system stores diagnostically relevant information and diagnostic information, typically for a large population of subjects and practitioners. The back-end system generates system generated diagnoses and/or suggested remedial actions based on submitted inquiries or requests. The back-end system can advantageously employ machine learning techniques to identify correlations between defining characteristics or features of pulse waveforms and diagnoses, over a large number of samples submitted by a substantial number of practitioners, for instance of traditional Chinese medicine. The back-end system can also employ primary and/or secondary symptoms in identifying correlations.

21 Claims, 15 Drawing Sheets

(51) Int. Cl.
  *A61B 5/00*   (2006.01)
  *A61B 5/0402* (2006.01)
  *G16H 50/20*  (2018.01)

(52) U.S. Cl.
  CPC .......... *A61B 5/6826* (2013.01); *A61B 5/7225* (2013.01); *A61B 5/7264* (2013.01); *A61B 5/7275* (2013.01); *A61B 5/0004* (2013.01); *A61B 5/02438* (2013.01); *A61B 5/6824* (2013.01); *A61B 5/7278* (2013.01); *A61B 5/7475* (2013.01); *G16H 50/20* (2018.01)

(56) References Cited

U.S. PATENT DOCUMENTS

| | | | | |
|---|---|---|---|---|
| 6,354,999 | B1 * | 3/2002 | Dgany | A61B 1/015 600/486 |
| 6,432,060 | B1 | 8/2002 | Amano | |
| 2004/0267141 | A1 | 12/2004 | Amano et al. | |
| 2006/0161225 | A1 * | 7/2006 | Sormann | A61B 5/0031 607/61 |
| 2009/0156945 | A1 * | 6/2009 | Baruch | A61B 5/0215 600/484 |
| 2010/0022895 | A1 * | 1/2010 | Kim | A61B 5/024 600/485 |
| 2012/0184861 | A1 | 7/2012 | Dhurandhar et al. | |
| 2013/0046191 | A1 | 2/2013 | Lin et al. | |
| 2016/0256116 | A1 * | 9/2016 | Baik | A61B 5/7278 |
| 2016/0287110 | A1 * | 10/2016 | Morris | A61B 5/02416 |
| 2018/0168466 | A1 * | 6/2018 | Fan | A61B 5/02416 |

OTHER PUBLICATIONS

Written Opinion, dated Nov. 30, 2015, for PCT/US2015/046386, 11 pages.

* cited by examiner

AUTOMATED DIAGNOSIS BASED AT LEAST IN PART ON PULSE WAVEFORMS

BACKGROUND

Technical Field

The present disclosure generally relates to diagnostic systems, methods and devices, and in particular to systems and methods that automate evaluation of data and rendering of a diagnosis based on the same.

Description of the Related Art

Many medical practitioners rely on pulse or palpation to assess a wellness of individuals or patients. For example, in Western medicine, physicians and other health care providers typically measure blood pressure and pulse rate as part of a standard or conventional physical examination. Measuring pulse rate typically requires a finger and a timer or clock. Measuring blood pressure typically requires an inflatable cuff and a sphygmomanometer. Typically two measurements are taken, systolic blood pressure and diastolic blood pressure, which represent the maximum and minimum pressure, typically in millimeters of mercury (mm Hg). In some instances, Western medical practitioners may measure other parameters which are somewhat indicative of various characteristics of blood flow, for example measuring electrical activity of a heart (i.e., electrocardiogram) via leads that are responsive to electromagnetic signals produced as part of the function of the heart.

Some practitioners of non-Western medicine rely more on measurement of pulse than practitioners of Western medicine. For example, practitioners of traditional Chinese medicine (TCM) often take a pulse of a patient and may render a diagnosis based at least in part, if not solely, on the patient's pulse. While such technique has likely been employed for over a thousand years, there tends to be a wide range in variability associated with such technique. For example, there is substantial variability in how one practitioner senses or interprets pulse relative to another practitioner, or even from day-to-day or patient-to-patient for a given practitioner. Likewise, there is substantial variability in resulting diagnoses between different practitioners given the same or very similar pulses, as well as variability in resulting diagnoses by a given practitioner given the same or very similar pulses.

BRIEF SUMMARY

While the use of pulse in performing diagnosis has proved useful, there is significant variability in how pulse is sensed or interpreted, and significant variability in the corresponding diagnoses. It is desirable to reduce such variability.

A system may include a device that has one or more sensors or transducers, which are operable to consistently sense or measure pulse waveforms, reducing or eliminating at least one source of variability. The system may collect a large number of sample pulse waveforms or pulse waveform information, along with sample diagnoses, to form a database or other collection of information, from which the system may determine or define correlations between defining characteristics of pulse waveforms and specific diagnoses and/or remedial or preventive measures and/or metrics of cardiac function. The system may further collect sample symptoms along with the sample pulse waveforms and sample diagnoses, from which the system may determine or define correlations between combinations of i) defining characteristics of pulse waveforms and ii) symptoms and specific diagnoses and/or remedial or preventive measures and/or metrics of cardiac function. The system may, for example, employ one or more machine-learning techniques or a neural network during a training time to determine or define the correlations.

The system includes sensors for the acquisition of various dynamic properties of a pulse (e.g., arterial pulse) that represent a functioning of a cardiovascular system of a subject, including a heart, blood, and vasculature, and the pulse's interaction and profusion through the blood vessels, tissue and organs. The system processes the collected signals, and generates diagnoses of various medical or health-related conditions, ailments and/or maladies.

During a runtime, the system may receive queries, for example in the form of pulse waveform information, with or without identified symptoms, and in response generate metrics of cardiac function and determine an appropriate diagnosis and/or remedial or preventive measures to recommend based on a set of accumulated knowledge or knowledge base and/or metrics of cardiac function. Thus, the system can autonomously produce or provide a diagnosis and/or recommended remedial or preventive measure based on pulse waveform information, with or without identified symptoms, using a set of accumulated knowledge or knowledge base.

The set of accumulated knowledge or knowledge base may be further improved using feedback from practitioners. The feedback can, for example, specify whether the diagnosis autonomously produced or provided by the system was correct, or if not, specifying what the correct diagnosis or remedial or preventive measure should have been for a given set of pulse waveform information, with or without a specified symptom.

During a runtime, the system may be used as a training tool, allowing a practitioner to sample pulse waveforms, with or without specified symptoms, diagnose the same, and compare the practitioner's diagnosis with that generated from a set of accumulated knowledge or knowledge base that spans a large group of subjects or patients and, preferably spans a large group of experienced practitioners. Such can provide appropriate feedback, allowing a practitioner to sharpen or improve their diagnostic skills.

The system employs a set of sensors or transducers to capture the pulse waveforms at one or more locations, for example at three locations along a radial artery of the subject or patient. The sensors or transducers capture the pulse waveforms at one, or preferably more, levels of applied force or pressure, at least of the locations. The system can employ a set of sensors or transducers to sense or measure the amount of applied force or pressure. The sensors or transducers that sense the pulse waveform may, for example, be separate and distinct from those that sense or measure the applied force or pressure. The system can employ a set of sensors or transducers to sense or measure electrical activity of the heart, for example one or more EKG leads. The system can use electrical activity as timing information for the pulse waveforms, for instance to implement noise filtering, enhancing the ability to identify certain defining characteristics of the pulse waveforms.

In at least one implementation, various back-end system functions can be provided under a software as a service (SaaS) model, using a Web interface or portal to submit queries or requests, and to receive responses including diagnoses, and/or providing training of practitioners. In at least one implementation, various back-end system functions can be provided via telemedicine service, allowing remote diagnosing, particularly where a subject is located far from a medical practitioner. In at least one implementation, various system functions can be provided in a clinic or emergency room, to quickly triage a subject or patient.

A diagnostic system may be summarized as including: at least one processor circuit; at least one nontransitory memory communicatively coupled the at least one processor circuit and which stores at least one of processor executable instructions or data, execution of which causes the at least one processor circuit to: for each of a number of visits by each of a plurality of subjects, receive respective pulse signal information representative of: i) a first pulse signal waveform captured from the respective subject at a first applied pressure at a first location and ii) at least a second pulse signal waveform captured from the respective subject a second applied pressure at the first location, the second applied pressure different than the first applied pressure, and receives diagnosis information that includes at least a primary diagnosis associated with the respective visit by the respective subject; store the received respective pulse signal information and diagnosis information to the at least one nontransitory memory; and determine one or more correlations between various ones of a number of defining characteristics of representations of the first and at least the second pulse signal waveforms and the diagnosis information. The system can receive, at leave one value indicative of at least one of the first or the second applied pressures, first instance a respective value indicative a level of force or pressure applied when sensing the first pulse signal waveform and when sensing the second pulse signal waveform.

The at least one processor circuit may receive the pulse signal information and the diagnosis information in anonymized form. For each of the number of visits by each of the plurality of subjects, the at least one processor circuit may receive respective pulse signal information representative of: iii) a third pulse signal waveform captured from the respective subject at a third applied pressure at the first location, the third applied pressured different from the first and the second applied pressures. For a given one of the visits of a given one of the subjects, the received respective pulse signal information may further represent a fourth, a fifth and a sixth pulse signal waveform captured from the respective subject at a first, a second and a third applied pressure, respectively, at a second location along a given artery, the second location spaced from the first location. For a given one of the visits of a given one of the subjects, the first, the second and the third pulse signal waveforms may be captured temporally proximate to one another. For a given one of the visits of a given one of the subjects, the first, the second, the third, the fourth, the fifth and the sixth pulse signal waveforms may be captured temporally proximate to one another. For the given one of the visits of the given one of the subjects, the first, the second and the third pulse signal waveforms may represent pulse waveforms captured at a first location along the radial artery proximate a wrist bone on a thumb side of a hand of the subject at the first, the second and the third applied pressures, respectively, and the fourth, the fifth, and the sixth pulse signal waveforms may represent pulse waveforms captured at a second location along the radial artery proximate the ulnar, at the first, the second and the third applied pressures, respectively, the second location spaced from the first location. For a given one of the visits of a given one of the subjects, the received respective pulse signal information may further represent a seventh, an eight and a ninth pulse signal waveform captured from the respective subject at a first, a second and a third applied pressure, respectively, at a third location along the radial artery, the third location closely spaced from the first and the second locations. For a given one of the visits of a given one of the subjects, the first, the second, the third, the fourth, the fifth, the sixth, the seventh, the eight, and the ninth pulse signal waveforms may be captured substantially concurrently with one another. The first, the second and the third pulse signal waveforms may each represent respective ones of pulse waveforms captured through a skin of the given subject. For at least a subset of the number of visits by at least a subset of the plurality of subjects the received diagnosis information may include at least a secondary diagnosis associated with the respective visit by the respective subject. For at least a subset of the number of visits by at least a subset of the plurality of subjects, the diagnostic system may receive at least a primary symptom associated with the respective visit by the respective subject. The at least one processor circuit may receive the pulse signal information and the diagnosis information in anonymized form. For at least a subset of the subset of visits by at least a subset of the subset of subjects, the diagnostic system may receive at least a secondary symptom associated with the respective visit by the respective subject. For at least a subset of the number of visits by at least a subset of the plurality of subjects the received diagnosis information may include at least a secondary diagnosis associated with the respective visit by the respective subject. The at least one processor circuit may perform machine learning on the pulse waveform and diagnosis information during a training time to determine one or more correlations between various ones of a number of defining characteristics of representations of the first and at least the second pulse signal waveforms and the diagnosis information. During a runtime, the runtime following the training time, for each of a plurality of additional visits, the at least one processor circuit may receive pulse waveform information for the respective visit and respective subject, and may determine a diagnosis based at least in part on the received pulse waveform information and the determined correlations, and may provide the determined diagnosis. During a runtime, the runtime following the training time, for each of a plurality of additional visits, the at least one processor circuit may receive pulse waveform information and symptom information for the respective visit and respective subject, and may determine the diagnosis based at least in part on the received pulse waveform information, the symptom information and the determined correlations, and may provide the determined diagnosis. During the runtime, the at least one processor circuit may receive the pulse signal information and the diagnosis information in anonymized form. Execution of the at least one of processor executable instructions or data at least one nontransitory memory may cause the at least one processor circuit to, for each of the number of visits by each of the plurality of subjects, receive timing information which represents an event in a cardiac cycle that is sensed separately from the plurality of pulse waveforms. The timing information may represent an electrocardiogram (EKG) signal sensed with an EKG transducer, the pulse signal waveforms being delayed with respect to the electrocardiogram (EKG) signal by a known range of time. The at least one processor circuit may further identify at least one identifying characteristic in at least one of the pulse signal waveforms based at least in part on the timing information, for each of at least a subset of the number of visits by each of at least a subset of the plurality of subjects. Execution of the at least one of processor executable instructions or data at least one nontransitory memory may cause the at least one processor circuit to, for each of the number of visits by each of the plurality of subjects, receive electrocardiogram timing information which represents an event in a cardiac cycle that is sensed separately from the plurality of pulse waveforms; and the at least one processor circuit may further identify at least one identifying characteristic in at least one of the pulse signal waveforms based at least in part on the timing information, for each of at least a subset of the number of visits by each of at least a subset of the plurality of subjects. The received respective pulse signal information may represent digitized versions of the first and the second pulse signal waveforms. The at least one processor circuit may digitize the first and second pulse signal waveforms to generate the respective pulse signal information.

A method operation in a diagnostic system that includes at least one processor circuit and at least one nontransitory memory communicatively coupled the at least one processor circuit and which stores at least one of processor executable instructions or data may be summarized as including: for each of a number of visits by each of a plurality of subjects, receiving respective pulse signal information representative of: i) a first pulse signal waveform captured from the respective subject at a first applied pressure at a first location and ii) at least a second pulse signal waveform captured from the respective subject a second applied pressure at the first location, the second applied pressure different than the first applied pressure, and receives diagnosis information that includes at least a primary diagnosis associated with the respective visit by the respective subject; storing the received respective pulse signal information and diagnosis information to the at least one nontransitory memory; and determining one or more correlations between various ones of a number of defining characteristics of representations of the first and at least the second pulse signal waveforms and the diagnosis information. The method can include sensing or receiving, at leave one value indicative of at least one of the first or the second applied pressures, first instance a respective value indicative a level of force or pressure applied when sensing the first pulse signal waveform and when sensing the second pulse signal waveform.

Receiving the pulse signal information and the diagnosis information may include receiving the pulse signal information and the diagnosis information in anonymized form. For each of the number of visits by each of the plurality of subjects, receiving the respective pulse signal information may include receiving the pulse signal information representative of: iii) a third pulse signal waveform captured from the respective subject at a third applied pressure at the first location, the third applied pressured different from the first and the second applied pressures. For a given one of the visits of a given one of the subjects, the received respective pulse signal information may further represent a fourth, a fifth and a sixth pulse signal waveform captured from the respective subject at a first, a second and a third applied pressure, respectively, at a second location along a given artery, the second location spaced from the first location. For a given one of the visits of a given one of the subjects, the first, the second and the third pulse signal waveforms may be captured temporally proximate to one another. For a given one of the visits of a given one of the subjects, the first, the second, the third, the fourth, the fifth and the sixth pulse signal waveforms may be captured temporally proximate to one another. For the given one of the visits of the given one of the subjects, the first, the second and the third pulse signal waveforms may represent pulse waveforms captured at a first location along the radial artery proximate a wrist bone on a thumb side of a hand of the subject at the first, the second and the third applied pressures, respectively, and the fourth, the fifth, and the sixth pulse signal waveforms may represent pulse waveforms captured at a second location along the radial artery proximate the ulnar, at the first, the second and the third applied pressures, respectively, the second location spaced from the first location. For a given one of the visits of a given one of the subjects, the received respective pulse signal information may further represent a seventh, an eight and a ninth pulse signal waveform captured from the respective subject at a first, a second and a third applied pressure, respectively, at a third location along the radial artery, the third location closely spaced from the first and the second locations. For a given one of the visits of a given one of the subjects, the first, the second, the third, the fourth, the fifth, the sixth, the seventh, the eight, and the ninth pulse signal waveforms may be captured substantially concurrently with one another. The first, the second and the third pulse signal waveforms may each represent respective ones of pulse waveforms captured through a skin of the given subject. For at least a subset of the number of visits by at least a subset of the plurality of subjects the received diagnosis information may include at least a secondary diagnosis associated with the respective visit by the respective subject. For at least a subset of the number of visits by at least a subset of the plurality of subjects, the method may include receiving at least a primary symptom associated with the respective visit by the respective subject. Receiving the pulse signal information and the diagnosis information may include receiving the pulse signal information and the diagnosis information in anonymized form. For at least a subset of the subset of visits by at least a subset of the subset of subjects, the method may include receiving at least a secondary symptom associated with the respective visit by the respective subject. For at least a subset of the number of visits by at least a subset of the plurality of subjects the received diagnosis information may include at least a secondary diagnosis associated with the respective visit by the respective subject. The method may further include: performing machine learning on the pulse waveform and diagnosis information during a training time, by the at least one processor circuit, to determine one or more correlations between various ones of a number of defining characteristics of representations of the first and at least the second pulse signal waveforms and the diagnosis information. During a runtime, the runtime following the training time, for each of a plurality of additional visits, the method may include receiving, by the at least one processor circuit, pulse waveform information for the respective visit and respective subject, and determining, by the at least one processor circuit, a diagnosis based at least in part on the received pulse waveform information and the determined correlations, and provides the determined diagnosis. During a runtime, for each of a plurality of additional visits, the at least one processor circuit can receive pulse waveform information and symptom information for the respective visit and respective subject, determine the diagnosis based at least in part on the received pulse waveform information, the symptom information and the determined correlations, and provide the determined diagnosis. During the runtime, the method can include receiving the pulse waveform information for the respective visit and respective subject may include pulse waveform information for the respective visit and respective subject in anonymized form. The method may further include: for each of the number of visits by each of the plurality of subjects, receiving, by the at least one processor circuit, timing information which represents an event in a cardiac cycle that is sensed separately from the plurality of pulse waveforms. The timing information may represent an electrocardiogram (EKG) signal sensed with an EKG transducer, the pulse signal waveforms being delayed with respect to the electrocardiogram (EKG) signal by a known range of time. The method may further include: identifying, by the at least one processor circuit, at least one identifying characteristic in at least one of the pulse signal waveforms based at least in part on the timing information, for each of at least a subset of the number of visits by each of at least a subset of the plurality of subjects. The method may further include: for each of the number of visits by each of the plurality of subjects, receiving electrocardiogram timing information which represents an event in a cardiac cycle that is sensed separately from the plurality of pulse waveforms; and identifying, by the at least one processor circuit, at least one identifying characteristic in at least one of the pulse signal waveforms based at least in part on the timing information, for each of at least a subset of the number of visits by each of at least a subset of the plurality of subjects. The receiving respective pulse signal information may include receiving respective pulse signal information that represents digitized versions of the first and the second pulse signal waveforms. The method may further include: digitizing the first and second pulse signal waveforms, by the at least one processor circuit, to generate the respective pulse signal information.

A system to capture diagnostic information may be summarized as including: a device, the device comprising: a first pulse waveform transducer response to a pulse to produce a first pulse waveform representation; a second pulse waveform transducer response to a pulse to produce a second pulse waveform representation, the second pulse waveform transducer spaced in use from the first pulse waveform transducer; and at least one applied pressure transducer responsive to an applied pressure of at least the first pulse waveform transducer and which in response to the applied pressure produces a pressure signal proportional to the applied pressure.

The system may further include: a number of couplers that carries the first and the second pulse waveform transducers, and the at least one applied pressure transducer, the couplers selectively attachable and detachable to a number of fingers of a clinician. The system may further include: a sleeve or cuff that carries the first and the second pulse waveform transducers, and the at least one applied pressure transducer, the sleeve or cuff selectively attachable and detachable to a wrist of the subject. The system may further include: a third pulse waveform transducer response to a pulse to produce a third pulse waveform representation, the third pulse waveform transducer spaced in use from the first and the second pulse waveform transducer. The system may further include: a number of couplers that carries the first, the second, and the third pulse waveform transducers, and the at least one applied pressure transducer, the couplers selectively attachable and detachable to position the first, the second, and the third pulse waveform transducers on respective ones of a plurality of fingertips of a clinician. At least one applied pressure transducer may include: a first applied pressure transducer positioned to respond to pressure applied via the first pulse waveform transducer; a second applied pressure transducer positioned to respond to pressure applied via the second pulse waveform transducer: a third applied pressure transducer positioned to respond to pressure applied via the third pulse waveform transducer. The system may further include: a number of couplers that carries the first, the second, and the third pulse waveform transducers, and the first, the second and the third applied pressure transducer, the couplers selectively attachable and detachable to position the first, the second, and the third pulse waveform transducers on respective ones of a plurality of fingertips of a clinician. The system may further include: a user input device that in use receives information that specifies at least a primary diagnosis. The system may further include: a user input device that in use receives information that specifies at least a primary symptom. The user input device may further receive information that specifies at least a primary diagnosis. The user input device may further receive information that specifies at least a secondary diagnosis. The user input device may further receive information that specifies at least a secondary symptom. The system may further include: at least one communications port that transmits at least the first and the second pulse waveform representation and the pressure signal proportional to the applied pressure from the system.

A method of operation in a system to capture diagnostic information may be summarized as including: producing a first pulse waveform representation that represents a first pulse waveform detected by a first pulse waveform transducer at a first location along a first artery and a first applied pressure; producing a second pulse waveform representation that represents a second pulse waveform detected by a second pulse waveform transducer at a second location along the first artery and a first applied pressure, the second location spaced from the first location; producing at least a first applied pressure signal proportional to the applied pressure of at least the first pulse waveform transducer; and transmitting the first pulse waveform representation, the second pulse waveform representation and at least a first applied pressure signal from diagnostic device.

The method may further include: producing a first pulse waveform representation that represents the first pulse waveform detected by a first pulse waveform transducer at the first location along the first artery and a second applied pressure, the second applied pressure different than the first applied pressure; producing a second pulse waveform representation that represents a second pulse waveform detected by a second pulse waveform transducer at the second location along the first artery and a second applied pressure, the second applied pressure different than the first applied pressure. The method may further include: producing a first pulse waveform representation that represents the first pulse waveform detected by a first pulse waveform transducer at the first location along the first artery and a third applied pressure, the third applied pressure different than the first and the second applied pressure; producing a second pulse waveform representation that represents a second pulse waveform detected by a second pulse waveform transducer at the second location along the first artery and a third applied pressure, the third applied pressure different than the first and the second applied pressure. The method may further include: producing a third pulse waveform representation that represents a third pulse waveform detected by a third pulse waveform transducer at a third location along a first artery and a first applied pressure, the third location different from the first and the second locations. The method may further include: producing a third pulse waveform representation that represents a third pulse waveform detected by a third pulse waveform transducer at the third location along the first artery and at a second applied pressure, the second applied pressure different than the first applied pressure. Producing at least a first applied pressure signal proportional to the applied pressure of at least the first pulse waveform transducer may include producing a second and a third applied pressure signal proportional to the applied pressure of the second and the third pulse waveform transducers, respectively. The method may further include: receiving information that specifies at least a primary diagnosis via at least one user input device. The method may further include: receiving information that specifies at least a primary symptom via at least one user input device. The method may further include: receiving information that specifies at least a primary symptom via at least one user input device. The method may further include: receiving information that specifies at least a secondary diagnosis via at least one user input device. The method may further include: receiving information that specifies at least a secondary symptom via at least one user input device. The method may further include: transmitting the received information that specifies at least a primary symptom and at least a primary symptom along with the first pulse waveform representation, the second pulse waveform representation and at least a first applied pressure signal from diagnostic device.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

DETAILED DESCRIPTION

Figure 1:
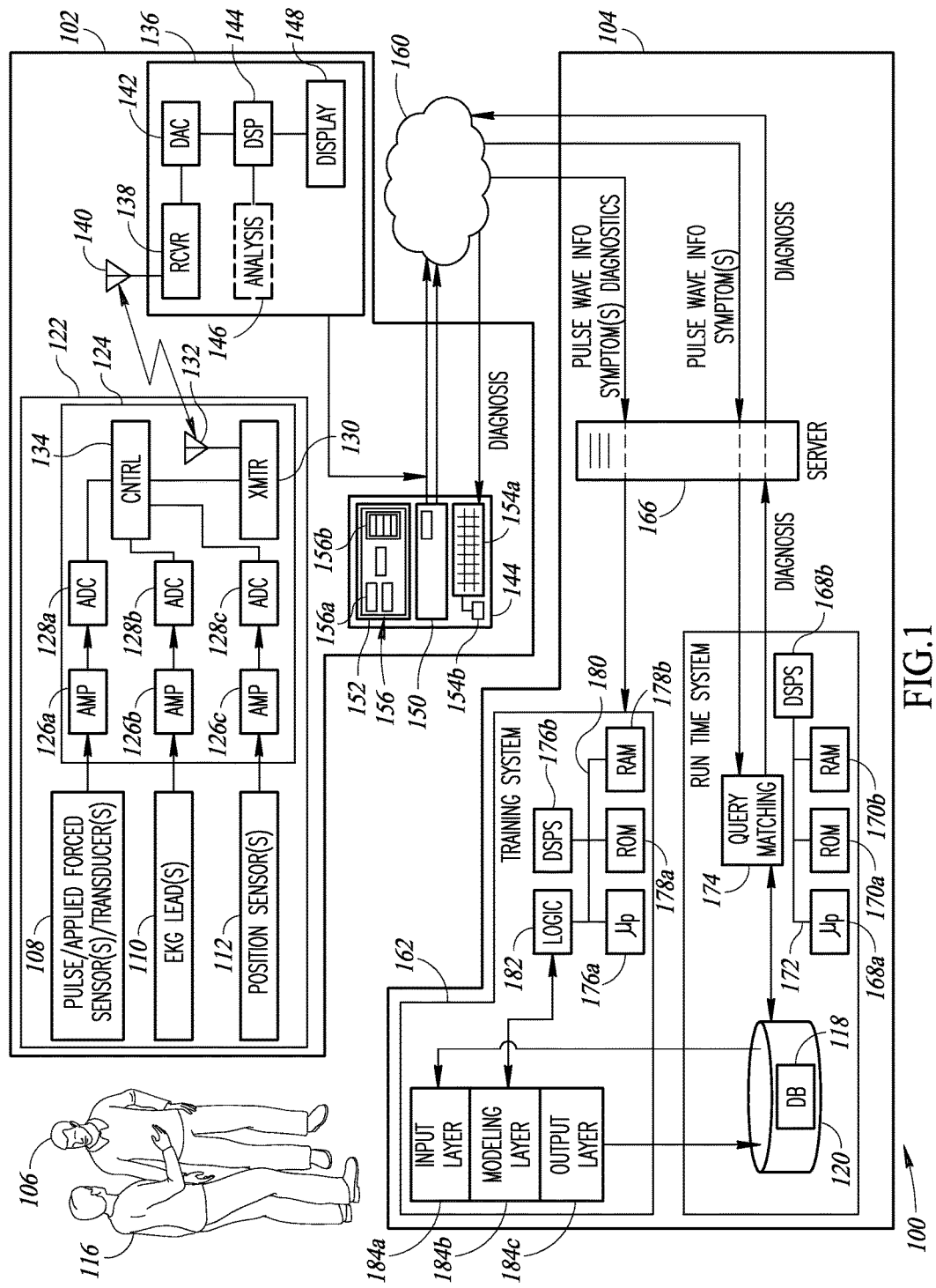
FIG. 1 is a schematic diagram illustrating an example diagnostic system that includes one or more front end subsystems and one or more back-end systems, for example a machine-learning system, according to one illustrated implementation.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations. In other instances, well-known mathematical, statistical or machine-learning methods for performing analyses and other well-known mathematical operations have not been described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the implementations.

Implementations of the present disclosure reduce or eliminate variability in interpreting sensed or measured pulse waveforms, and in rendering diagnoses based at least in part on the sensed or measured pulse waveforms, and in at least some instances on symptoms (e.g., reported or observed primary symptoms, reported or observed secondary symptoms). The system may generate diagnostic models that correlate pulse waveform information, and optionally symptoms, with diagnoses and/or suggested remedial or preventive measures and/or generate metrics of cardiac function.

Using a plurality of samples of pulse waveforms and practitioner diagnoses associated with respective pulse waveforms, a diagnostic model is generated using a machine-learning system that can: i) identify defining characteristics of pulse waveforms, and/or ii) autonomously provide diagnoses based on received pulse waveforms using a set of accumulated knowledge or knowledge base. The set of accumulated knowledge or knowledge base spans a large group of subjects or patients, and preferably spans a large group of experienced practitioners. The diagnoses can be with respect to various medical or other conditions, ailments and/or maladies. The rate and strength of a pulse can, for example, be used to determine or assess levels of hydration, arterial blockage, levels of fitness, systolic blood pressure, heart failure, hypertrophic obstructive cardiomyopathy, hyperdynamic circulation, cardiac tamponade, pericarditis, chronic sleep apnea, croup, and/or obstructive lung disease. A weak and delayed pulse may indicate severe aortic stenosis. A bifid systolic pulse may be indicative of some obstructive cardiomyopathies. A bounding pulse typically indicates a large stroke volume with a rapid fall-off, which can occur in hyperkinetic states, such as a fever, anemia and/or thyrotoxicosis. Assessable conditions can, for example, include hydration, or hunger or consumption. For example, a second reflection in the pulse wave (i.e., superior mesenteric) can be indicative of hunger. Such can be used to provide information to people who are dieting. Such can be used to provide to parents or caregivers of an infant or other individual (e.g., stroke victim) who is uncommunicative and cannot otherwise clearly indicate that they are hungry.

The system can used as a training tool, allowing a practitioner to sample pulse waveforms, with or without specified symptoms, diagnosis the same, and compare the practitioner's diagnosis with that generated from a set of accumulated knowledge or knowledge base that spans a large group of subjects or patients and, preferably spans a large group of experienced practitioners. Such can provide appropriate feedback, allowing a practitioner to sharpen or improve their diagnostic skills.

For instance, each of the components of the diagnostically relevant data can be converted into an input readable by a binary search tree algorithm or other machine-learning algorithm. Diagnostically relevant data can include pulse waveforms or information that specifies various values of defining characteristics of pulse waveforms. Diagnostically relevant data can optionally include one or more primary symptoms or secondary symptoms reported by a subject or observed by a practitioner. Diagnostically relevant data can optionally include one or more primary diagnoses or secondary diagnoses provided by a practitioner. In some instances, the primary diagnoses or secondary diagnoses may be preliminary, where the practitioner is attempting to confirm the primary diagnoses or secondary diagnoses via the system.

The binary search tree may take the available information and divide the data into two branches based on the split of a single linear or categorical variable that places the most first diagnosis examples on one branch, and the most second diagnosis examples on the other branch. The binary search tree algorithm may then repeat for each newly created branch until reaching a stopping condition. Stopping conditions are defined so that the tree does not over fit the data. In this particular example, the stopping criteria may be defined by the minimum number of elements that a final branch ("leaf") is allowed to contain. This is highly dependent upon the size of the dataset. A second stopping criteria, complexity, may be defined such that the R-squared of the model, a statistical measure of how close the data fits the model, must increase by a certain amount for a split to be considered. The tree may also be generated using cross validation to help ensure that the tree is not overfitting. Once generated, the tree may be pruned, again based on complexity and fit, in order to reduce overfitting. Other classification methods like support vector machines, boosted trees, neural networks, Bayesian networks, or random forests may also be used.

As discussed in further detail below, the model may be used in at least two different situations. First, when a practitioner has collected diagnostically relevant information for a subject, and would like the system to generate one or more primary diagnoses or secondary diagnoses based on the diagnostically relevant information. Second, when a practitioner has collected diagnostically relevant information for a subject, and has made a preliminary primary diagnosis and/or preliminary secondary diagnosis, and would like to confirm that the practitioner's preliminary diagnosis is consistent with what other practitioners would diagnosis.

FIG. 1 shows an example diagnostic system 100 that includes a front-end system 102 and a back-end system computer system 104. The front-end system 102 collects diagnostically relevant information about a plurality of subjects 106 (only one shown) via respective sensors or transducers 108, 110, 112 and at least one user interface system 114. The front-end system(s) 102, or components thereof, can be operated by one or more medical practitioners 116 (only one shown), for example practitioners of traditional Chinese medicine. The back-end system computer system 104 forms a set of accumulated knowledge or knowledge base 118 stored in or on one or more nontransitory process-readable media 120, and can provide or generate metrics of cardiac function and/or diagnoses and/or suggested remedial or preventive measures in response to queries generated by the front-end systems 102.

While illustrated as a single front-end system 102, a typical implementation includes a plurality of front-end systems 102. The front-end system(s) 102 may be located at various respective clinical facilities or other locations. Likewise, while only a single subject 106 and single practitioner 116 are illustrated, in a typical implementation there are a plurality of subjects 106 and practitioners 116. For example, there may be two, ten, hundreds, thousands, or even hundreds of thousands of practitioners 116, each operating respective front-end systems 102. Each of the practitioners 116 may employ the respective front-end systems 102 on one or more of their patients or subjects 106. Thus, front-end systems 102 may collect diagnostically relevant information from tens, hundreds, thousands, hundreds of thousands or even millions of subjects. The back-end system computer system 104 forms the set of accumulated knowledge or knowledge base 118 that spans a large group of patients or subjects 106 and, preferably spans a large group of experienced practitioners 116. This large sampling pool allows advantageous use of machine-learning techniques to reduce variability in generating metrics of cardiac function and/or generating diagnoses and/or suggested remedial or preventive measures. The subjects 106 form a total population that includes various subjects or patients seeking treating from one or more medical practitioners 116, for example practitioners of traditional Chinese medicine and/or practitioners of Western style medicine.

The front end system 102 includes a subject interface device 122 that includes the one or more sensors or transducers 108, 110, 112. As described elsewhere herein, the subject interface device 122 may, for example, be worn by a practitioner 116 when examining a subject 106. Also as described elsewhere herein, the subject interface device 122 may, for example, be worn by a subject 106 when being examined by a practitioner 116.

The subject interface device 122 of the front end system 102 includes the one or more sensors or transducers 108 which are responsive to pulse waveforms, and optionally responsive to applied force or pressure.

The subject interface device 122 of the front end system 102 optionally includes one or more sensors or transducers 110 which are responsive to electrical activity, for example electrical activity of a heart of the subject 106, hence are denominated herein as electrocardiogram (EKG) sensors or transducers 110. The subject interface device 122 of the front end system 102 optionally includes, for example, a capacitive sensing array, positioned over a heart of a subject 106, to capture motion of individual portions (e.g., right ventricle, left ventricle, right aorta, left aorta) of the heart.

The subject interface device 122 of the front end system 102 optionally includes one or more sensors or transducers 110 which are responsive to position and/or orientation, hence are denominated herein as position or orientation transducers 112.

The subject interface device 122 of the front end system 102 optionally includes electronics 124 that perform preprocessing on signals from the various sensors or transducers. The electronics 124 may, for example, include one or more amplifiers 126a, 126b, 126c (three shown, collectively 126), for example analog signal amplifiers, coupled to receive and amplify signals from the various sensors or transducers 108, 110, 112. The electronics 124 may, for example, include one or more analog-to-digital converters (ADCs) 128a, 128b, 128c (three shown, collectively 128), which convert the amplified signals from analog to digital form.

The electronics 124 includes one or more communications ports (e.g., tethered or wired ports, wireless ports). As illustrated, the communications port preferably takes the form of one or more radios, transmitters, receivers or transceivers 130 and associated antenna(s) 132 which provides wireless communications from subject interface device 122. Such allows the subject interface device 122 to be conveniently worn by either the practitioner 116 or subject 106 during use.

The electronics 124 optionally includes a controller 134 (e.g., microcontroller or multiplexer) communicatively coupled to control the transmission of collected information from the subject interface device 122.

The front end system 102 includes a communications interface module 136 communicatively coupled to the subject interface device 122 to at least receive information from the sensors or transducers 108, 110, 112. Thus, communications interface module 136 includes one or more communications ports (e.g., wired ports, wireless ports). As illustrated, the communications port preferably takes the form of one or more radios, transmitters, receivers or transceivers 138 and associated antenna(s) 140 which provides wireless communications from the subject interface device 122.

The communications interface module 136 can optionally include a digital-to-analog (DAC) converter 142 coupled to receive digital signals from the radios, transmitters, receivers or transceivers 138 and convert the signals to analog form. The communications interface module 136 can optionally include one or more signal processors 144, for instance one or more digital signal processors (DSPs), or other signal processors (e.g., microprocessor, application specific integrated circuit (ASIC), field programmable gate array (FPGA), graphics processing unit (GPU), etc. The signal processors 144 can optionally perform analysis 146 on the received signals. For example, the signal processors 144 can analyze pulse waveforms in analog form for certain defining characteristics. Defining characteristics can take a variety of forms, for example: i) pulse transit time, i.e., between heart contraction and detection of pulse; ii) a global maxima in the pulse waveform; iii) global minima in the pulse waveform; iv) one or more local global maxima in the pulse waveform; v) one or more local minima in the pulse waveform; vi) one or more gradients in the pulse waveform between various distinctive waveform features (e.g., between a global maxima and a most immediately subsequent local maxima or local minima in the pulse waveform). Such may be characteristic of a health of various bodily functions, for instance: blood flow dynamics including strength of heart, arterial stiffness cardiac efficiency, and/or blood viscosity. Analysis may advantageously employ timing information, for instance EKG information that indicates electrical activity of the heart. Such allows the signal processors 144 to more readily discern signal from noise (e.g., normal variation across the population, noise introduced by movement of sensors or transducers, movement of subject and/or practitioner, practitioner's own pulse). For example, the timing information can be used as a timing reference for averaging a pulse pressure waveform signal to address noise introduced by involuntary movement of either the subject or practitioner, or introduced by physical activity of the subject, for instance undergoing a cardiac stress test.

The resulting information may be packaged or otherwise associated with other diagnostically relevant information (e.g., symptoms) to be transmitted to the back-end system computer system 104. In some instances, the defining characteristics may be sent to the back-end system computer system 104 without the underlying pulse waveforms from which the defining characteristics were derived. Such may advantageously limit an amount of information required to be sent or transmitted.

The communications interface module 136 can optionally include a display driver 148, which is communicatively coupled to drive a display or monitor 152 (discussed below) of the user interface system 114, for instance to present to a practitioner 116 various captured pulse waveforms for a particular subject 106.

As previously noted, the front end system 102 includes at least one user interface system 114. The user interface system 114 allows the practitioner to enter relevant diagnostic information. The user interface system 114 may, for example, include a processor-based computer system 150, with an output device or input/output device (e.g., display, monitor, screen, or touch sensitive screen) 152, an input device (e.g., keyboard or keypad 154a, cursor control such as mouse 154b, trackball, trackpad). The processor-based computer system 150 can take any of a large variety of forms, for instance workstation computers, desktop computers, laptop computers, tablet computers, netbook computers, smartphones, and/or personal digital assistants. The processor-based computer system 150 includes at least one processor and at least one nontransitory processor-readable medium that stores instructions that cause the at least one processor to present a user interface, for instance a graphical user interface 156, to collect relevant diagnostic information. For example, the user interface 156 may have one or more user interface elements (e.g., fields 156a, pull down or drop down menus 156b, selection lists, dialog boxes, radio buttons), which allow the user (e.g., practitioner 106) to enter or select diagnostically relevant information. Diagnostically relevant information can, for example, include one or more primary symptoms, one or more secondary symptoms, one or more prior or previous treatments, one or more prior or previous diagnoses from a previous patient or subject 106 visit. Diagnostically relevant information can, for example, include one or more primary diagnoses and/or one or more secondary diagnoses from the current patient or subject 106 visit.

An operator (e.g., practitioner 116) can enter commands and information into the user interface system 114 using one or more input devices such as a single or multi-point touch screen interface or keyboard 154a and/or a pointing device such as a mouse 154b, and/or via a graphical user interface. Other input devices can include a microphone, joystick, game pad, tablet, scanner, etc. These and other input devices are communicably coupled to the system using an appropriate I/O interface such as a serial port interface that couples to the system bus, although other interfaces such as a parallel port, a game port or a wireless interface or a universal serial bus ("USB") can be used. A monitor 152 or other display device is coupled to the system bus, for instance via a video interface such as a video adapter. The user interface system 114 can include other output devices, such as speakers, printers, etc. Thus, the system can provide a visual and/or auditory representation of pulse (e.g., pressure versus time). This enables a practitioner 116 to see and hear what the practitioner feels through the sensors or transducers 108, providing validation and additional interpretation of the signals.

At least one of the user interface system 114 or the communications interface module 136 both are communicatively coupled to the back-end system computer system 104 via one or more communicative paths 160. In particular, the user interface system 114 and/or the communications interface module 136 are communicatively coupled to provide diagnostically relevant information to the back-end system computer system 104, and optionally to receive diagnoses from the back-end system computer system 104.

For example, the user interface system 114 and/or the communications interface module 136 can provide the back-end system computer system 104 with diagnostically relevant information such as pulse wave information, symptom information and/or diagnosis information.

The communicative paths 160 can take any of a large variety of forms, and typically do not comprise part of the system 100. For example, the communicative paths 160 can take the form of the Internet, an extranet, an intranet, a virtual private network, or a dedicated communication channel. The communicative paths 160 can include wired and wireless or optical portions. The communicative paths 160 may include terrestrial landlines, optical cables, and/or microwave transmission relays. The communicative paths 160 may include satellite communications, with appropriate ground stations, radios and antennas. There may be any variety of computers, switching devices, routers, bridges, firewalls and other devices in the communications paths between the front-end system 102 and the back-end system 104.

The pulse wave information can, for instance, take the form of one or more analog or digital representations of one or more pulse waveforms detected, sensed or measured from a subject 106. Alternatively or additionally, the pulse wave information can, for instance, take the form of one or more values for one or more defining characteristics or parameters of one or more pulse waveforms detected, sensed or measured from a subject 106.

The symptom information may take a variety of forms. For example, the symptom information can take the form of a description of one or more primary and/or secondary symptoms experienced by a subject 106. The primary and/or secondary symptoms may be reported by the subject 106, and/or may be observed by the practitioner 106. The primary and/or secondary symptoms may be entered in freeform text, for instance via a freeform text field 156a of a user interface 156. More preferably, the primary and/or secondary symptoms can be selected from a pull-down menu 156b that includes a fixed list of primary and/or secondary symptoms. Use of a fixed set of symptoms can increase the accuracy of later diagnoses generated by the system 100.

The diagnoses information may take a variety of forms. For example, the symptom information can take the form of a description of one or more primary and/or secondary diagnoses by the practitioner 116 for the specific subject 106. The primary and/or secondary diagnosis may be entered in freeform text, for instance via a freeform text field of a user interface. More preferably, the primary and/or secondary diagnosis can be selected from a fixed list of primary and/or secondary diagnoses. Use of a fixed set of diagnoses can increase the accuracy of later diagnoses generated by the system 100. The primary and/or secondary diagnosis may only be entered when collecting data or information for initially populating or training the system 100. Thus, some practitioners may not enter either a primary and/or secondary diagnosis, relying on the system 100 to generate such based on the other diagnostically relevant information provided. In other instances, the practitioner 116 may provide the primary and/or secondary diagnosis, even after the system 100 has been initially populated or trained. Such may allow the system to continue to improve its ability to produce accurate primary and/or secondary diagnoses. Such may additionally or alternatively allow the system to be used in training practitioners 106, for example providing feedback comparing the practitioner's initial primary and/or secondary diagnosis to a primary and/or secondary diagnosis generated by the system 100.

The back-end system computer system 104 can include a machine-learning or training system 162, a runtime system 164, the database 118 stored on one or more nontransitory controller-readable storage media 120, and/or an optional traffic server 166.

The traffic server 166 can control traffic flow, and optionally implement a firewall. In some implementations, the traffic server 166 may send certain traffic (e.g., training diagnosis relevant information or data) to the training system, and other traffic (e.g., inquiries or requests for a diagnosis including diagnosis relevant information or data) to the runtime system. Alternatively, the traffic server 166 may send all traffic (i.e., training diagnosis relevant information or data; inquiries or requests for a diagnosis including diagnosis relevant information or data) to the training system, and send only traffic that is an inquiry or request for a diagnosis to the runtime system.

In at least one implementation, the traffic server 166 of the back-end system 104 can provide functions as a software as a service (SaaS) model, using a Web interface or portal to submit queries or requests, and to receive responses including diagnoses. Services can be offered on a subscription bases, or a "pay as you go" basis. The system may provide credits to practitioners who help to initially build or populate the datasets, which can be redeemed against later submitted inquiries or requests. In at least one implementation, various back-end system functions can be provided via telemedicine service, allowing remote diagnosing, particularly where a subject is located far from a medical practitioner. In at least one implementation, various system functions can be provided in a clinic or emergency room, to quickly triage a subject or patient. Some implementations can even allow a subject to perform a self-examination, for instance using the sleeve or cuff implementations and a Web portal to enter symptoms and submit pulse waveform information, and in response receiving system generated diagnoses.

The traffic server 166 can include one or more program modules stored in a system memory, such as an operating system, one or more application programs, other programs or modules and program data. In some implementations, application programs in the form of processor-readable instructions executable by at least one processor, may include but are not limited to, instructions that cause the traffic server 166 to: facilitate communication (e.g., via a number of interactive and non-interactive Webpages) with the user processor-based devices (e.g., user interface system 114); automatically store one or more initial data sets that include diagnostically relevant information including values of identifying characteristics or features of pulse waveforms in a data store or database 118 residing on nontransitory processor-readable storage medium 120; and automatically or autonomously supply diagnoses to users in response to received inquiries or requests.

Application programs may include processor-executable instructions related to routine functionality such as the automatic establishment, maintenance, and updating of information related to electronic or digital documents or files, as well as privileges, permissions or authorizations to perform various acts on such electronic or digital documents or files such as reading, modifying, annotating, importing, and/or deleting. Other program modules may include instructions for handling security such as a password or other access protection and communications encryption. The system memory may also include communications programs, for example applications that cause the traffic server 166 to function as a Webserver to distribute Webpages to the practitioners 116. In at least some instances, such Webserver functionality is markup language based, such as Hypertext Markup Language (HTML), Extensible Markup Language (XML) or Wireless Markup Language (WML), and operates with markup languages that use syntactically delimited characters added to the data of a document to represent the structure of the document. A number of suitable servers may be commercially available such as those from Cisco, Hewlett-Packard, Apache, Mozilla, Google, Microsoft, and Apple.

The runtime system 164 can include one or more processors, for example, one or more microprocessors 168*a* (with one or more cores), digital signal processors (DSPs) 168*b*, graphic processing units (GPUs), central processing units (CPUs), application specific integrated circuits (ASICs), field programmable gate arrays (FPGAs), programmable logic controllers (PLCs), or the like (collectively 168). The runtime system 164 can include one or more nontransitory processor-readable media (collectively 170) communicatively coupled to the processors 168 via a bus 172 or other channel, which stores controller executable instructions and/or data. The nontransitory controller-readable storage media 170 may take any of a variety of forms, for example nonvolatile memory, volatile memory, read only memory (ROM) 170*a*, electrically erasable programmable read only memories (EEPROMs), flash memories, random access memory (RAM) 170*b*, static RAM, dynamic RAM, or spinning media, for instance magnetic disks or optical disks. The nontransitory controller-readable storage media 170 may, for example, store instructions or logic 172 that cause the one or more processors to execute a query matching function with respect to data stored in the database 120 or via an output layer ## of a model implemented by the machine-learning or training system 162.

The machine-learning or training system 162 can include one or more processors, for example, one or more microprocessors 176*a* (with one or more cores), digital signal processors (DSPs) 176*b*, graphic processing units (GPUs), central processing units (CPUs), application specific integrated circuits (ASICs), field programmable gate arrays (FPGAs), programmable logic controllers (PLCs), or the like (collectively 176). The machine-learning or training system 162 can include one or more nontransitory processor-readable media (collectively 178) communicatively coupled to the processors via a bus 180 or other channel, which stores controller executable instructions and/or data. The nontransitory controller-readable storage media 178 may take any of a variety of forms, for example nonvolatile memory, volatile memory, read only memory (ROM) 178*a*, electrically erasable programmable read only memories (EEPROMs), flash memories, random access memory (RAM) 178*b*, static RAM, dynamic RAM, or spinning media, for instance magnetic disks or optical disks. The nontransitory controller-readable storage media 178 may, for example, store instructions or logic 182 that cause the one or more processors to execute a machine-learning function with respect to data stored in a database 120 or other data structure, for example implemented as an input layer 184*a*, a modeling layer 184*b*, and an output layer 184*c*.

In some implementations, the runtime system 164 accumulates, sorts, and/or organizes diagnostic relevant data. In some implementations, at least some of the diagnostically relevant data may be logically associated with respective ones of the subjects 106, for example via a unique identifier or name. In other implementations, at least some of the diagnostically relevant data may be in anonymized form, and not logically associable to any specific one of the subjects 106. In other implementations, at least some of the diagnostically relevant data may be logically associated with respective ones of the subjects 106, while some may be in anonymized form. For example, some of the diagnostically relevant data may be collected for training purposes, thus may be received in in anonymized form. Some of the diagnostically relevant data may be submitted as part as a query or request to generate a diagnosis and/or suggested remedial or preventive measures and/or generate metrics of cardiac function. Such diagnostically relevant data may be logically associated with respective ones of the subjects 106. Alternatively, such may be received by the system 100 in anonymized form, yet associable to a particular subject 106 by a practitioner 116 who submitted the query or request.

In at least some instances, the runtime system 164 organizes diagnostically relevant data into an initial data set that is then used to create a training data subset and a test data subset. The runtime system 164 supplies at least the training data subset to the machine-learning or training system 162 via one or more networks or communications channels. The machine-learning or training system 162 receives the training data subset at an input layer 184a.

Using the diagnostically relevant data included in the training data subset, the machine-learning or training system 162 constructs a model in the modeling layer 184b. The output data generated by the modeling layer 184b is communicated to the output layer 184c of the machine-learning or training system 162. The output data includes at least data indicative of a relatively likely primary and/or secondary diagnosis based on a particular set of diagnostically relevant data (e.g., pulse wave information, optionally symptom information, optionally preliminary primary and/or secondary diagnosis information).

The runtime system 164 receives the output data from the output layer 184c of the machine-learning or training system 162 via a network or channel. The runtime system 164 can generate a response to a query or request, the response including one or more primary or secondary diagnoses for the particular subject 106. The runtime system 164 can transmit the response to the practitioner 116 who initiated the inquiry or response, for example via the traffic server 166 and user interface system 114, or via a mobile or handheld device, for instance a smartphone or tablet computer of the practitioner 116.

In some instances, after the machine-learning or training system 162 is trained using one or more training data subsets, the runtime system 164 can supply one or more test data subsets to the machine-learning or training system 162 to assess the accuracy of the model 184c constructed by the machine-learning or training system 162. In such instances, the runtime system 164 can receive all or a portion of the output data from the output layer 184c of the machine-learning or training system 162.

From time to time, the runtime system 164 scrapes or otherwise obtains diagnostically relevant data from the initial data set to generate at least one training data subset and at least one test data subset. The runtime system 164 provides all or a portion of the training data subset to the input layer 184a of the machine-learning or training system 162 to permit the construction of a predictive model within the modeling layer 184b. The training data subset includes diagnostically relevant data logically associated with any number of subjects 106 with diagnoses.

From time to time, the runtime system 164 can scrape data from the initial data set to create at least one updated training data subset. Periodically, or from time to time, the runtime system 164 can provide all or a portion of this at least one updated training data subset to the input layer 184a of the machine-learning or training system 162 to update the predictive model used by the machine-learning or training system 162. In at least some implementations, the provision of the updated training data subset and the generation of an updated predictive model may be executed as a background task by either or both the front-end system 102 and the machine-learning or training system 162.

At times, the composition of the training data subset may be representative of the initial data set used to form the training data subset. At other times, the composition of the training data subset may be skewed such that the composition of the training data subset is not representative of the composition of the initial data set used to form the training data subset.

At yet other times, it may be beneficial to weight one or more diagnostically relevant data attribute values included in the training data subset to favor the identification of diagnoses with such attribute values as more likely correct than the general population of diagnoses.

In some instances, after updating the predictive model using at least one updated training data subset, the accuracy of the updated predictive model is evaluated using all or a portion of at least one test data subset or all or a portion of at least one updated test data subset scraped from the initial data set. In some instances, the accuracy of the updated predictive model is assessed against one or more defined threshold value limits and/or one or more defined threshold value ranges.

While the machine-learning or training system 162 is depicted in FIG. 1 as including an input layer 184a, a modeling layer 184b, and an output layer 184c, other machine-learning system configurations are possible. The machine-learning or training system 162 can include one or more predictive models, including binary search trees, neural networks, random forests, or boosted trees. Additionally, although the machine-learning or training system 162 is depicted in FIG. 1 as separate from the runtime system 164, all or a portion of the machine-learning or training system 162 may be incorporated into the runtime system 164, or even into the front-end system 102. Additionally, the front-end system 102 and the back-end system computer system 104 may be integrated into a single system, or distributed as two or more physical and/or logical systems.

The machine-learning or training system 162 can be separate, partially included, or completely included within the runtime system 164. In other words, in some instances, although described herein in the context of different, discrete devices, the processor of the runtime system 164 may be the same as the processor of the machine-learning or training system 162. Similarly, although described herein in the context of different, discrete devices, the nontransitory processor-readable storage media of the runtime system 164 may be the same as the nontransitory processor-readable storage media of the machine-learning or training system 162. The machine-learning or training system 162 receives output data from the output layer 146 of the machine-learning or training system 162. The output data includes at least one value indicative of a relative likely diagnosis.

A predictive model can include one or more binary search trees within the modeling layer 184a. Each of the values of the various characteristics of the pulse waveform may be converted into an input readable by a binary search tree algorithm or other machine-learning algorithm. The binary search tree may take the available information and divide the data into two branches based on the split of a single linear or categorical variable that places samples with a first set of common values for a first or high level pulse waveform characteristic on one branch, and samples with a second set of common values for the first or high level pulse waveform characteristic on the other branch. The binary search tree algorithm may then repeat for each newly created branch until reaching a stopping condition. Each branch may address a refinement in value for the particular pulse waveform characteristic. Each branch may address a different pulse waveform characteristic. Each branch may address a respective symptom, either a primary or a secondary symptom. Stopping conditions are defined so that the tree does not over fit the data. In this particular example, the stopping criteria may be defined by the minimum number of elements that a final branch ("leaf") is allowed to contain. This is highly dependent upon the size of the dataset. A second stopping criteria, complexity, may be defined such that the R-squared of the model, a statistical measure of how close the data fits the model, must increase by a certain amount for a split to be considered. The tree may also be generated using cross validation to help ensure that the tree is not overfitting. Once generated, the tree may be pruned, again based on complexity and fit, in order to reduce overfitting.

As another example, in some implementations the machine-learning or training system 162 can include a predictive model including one or more neural networks within the modeling layer 184b. Connections within the one or more neural networks are formed and/or re-formed using at least in part, the attribute value data associated with diagnostically relevant information and corresponding diagnoses included in the training data subset. Connection weights within the one or more neural networks are established or re-established using, at least in part, the attribute value data associated with the subjects having submitted or known diagnoses included in the training data subset. In some implementations, the runtime system 164 provides the training data subset to the input layer 184a of the machine-learning or training system 162 until output data received from the output layer 184c of the machine-learning or training system 162 indicates one or more performance aspects of the machine-learning system has plateaued. In some implementations, the runtime system 164 determines whether the one or more performance aspects have plateaued based at least in part on whether a defined number of machine-learning system training epochs have been reached.

Other classification methods, such as support vector machines, boosted trees, or random forests may also be used.

Once trained, the machine-learning or training system 162 provides an accurate and reliable primary and/or secondary diagnosis based on diagnostically relevant data attribute values logically associated with the particular user. Even more advantageously, updating the predictive model from time to time with current known diagnostically relevant information and corresponding diagnoses, improves predictive performance.

In some implementations, the runtime system 164 can include one or more media, service, or content delivery devices, for example one or more Webservers delivering content in the form of diagnoses and/or practitioner training or feedback. The content, in the form of audio, video, or audio/video data may be delivered to any number of processor-based user interface systems 114, each of which is associated with a respective practitioner 116. The processor-based user interface systems 114 can include any device suitable for receiving content from the service provider such as a desktop computer, portable or laptop computer, smartphone, wearable computer or the like.

Figure 2A:
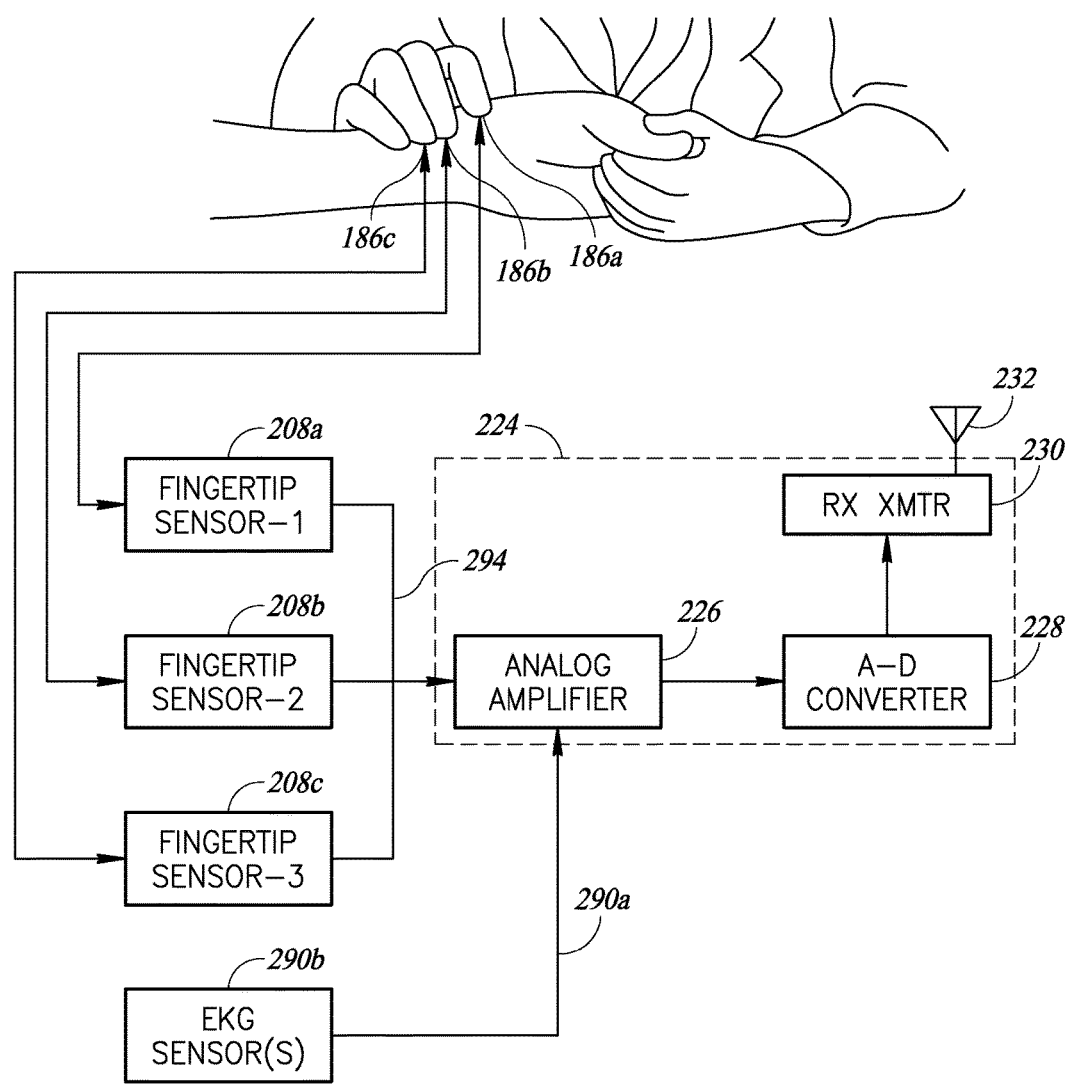
FIG. 2A is a schematic view of a subject interface device to capture pulse waveform signals from a subject, according to one illustrated implementation.
Figure 2B:
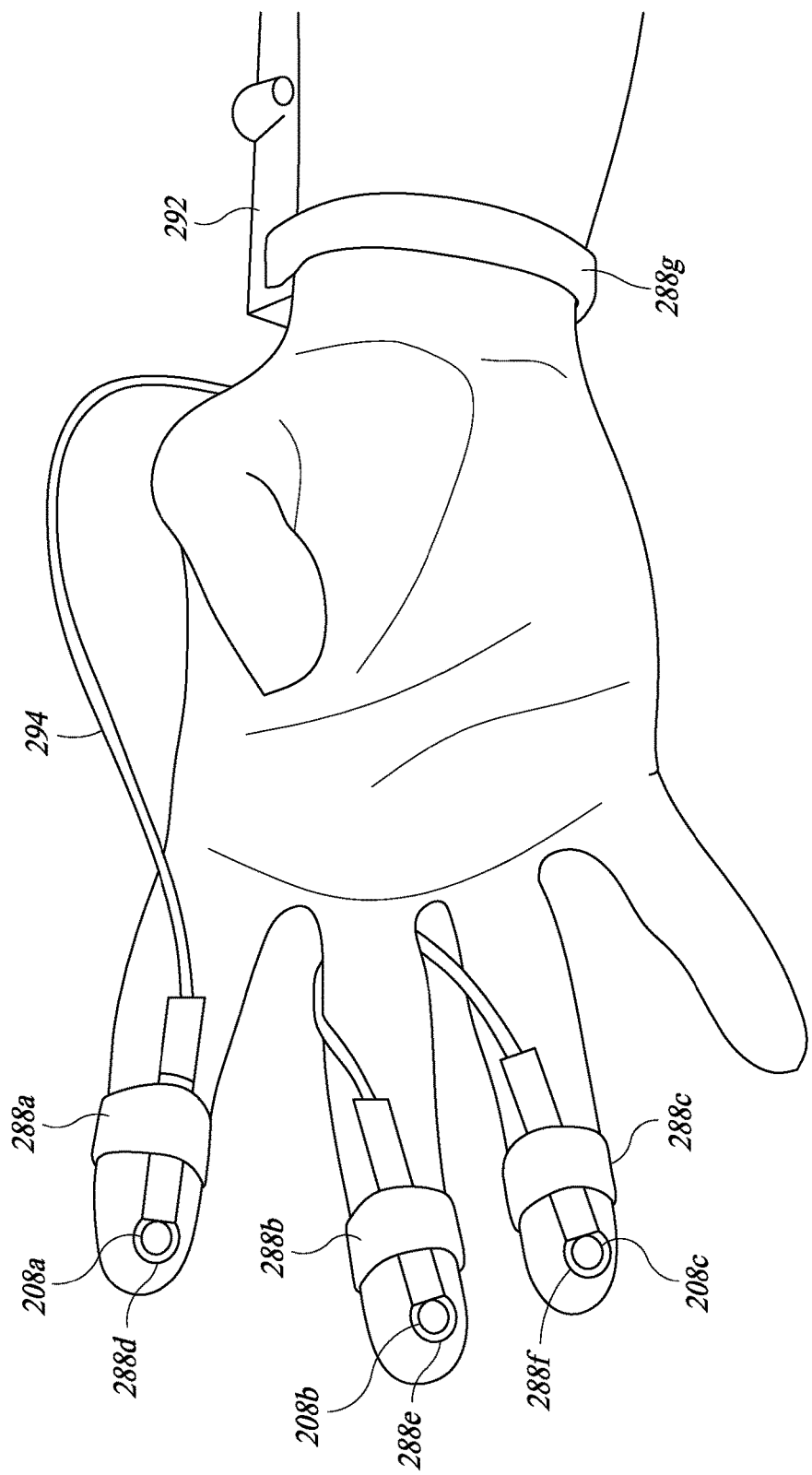
FIG. 2B is a front plan view of the subject interface device of FIG. 2A shown mounted on a hand and arm of an individual, for example a practitioner, according to one illustrated implementation.
Figure 2C:
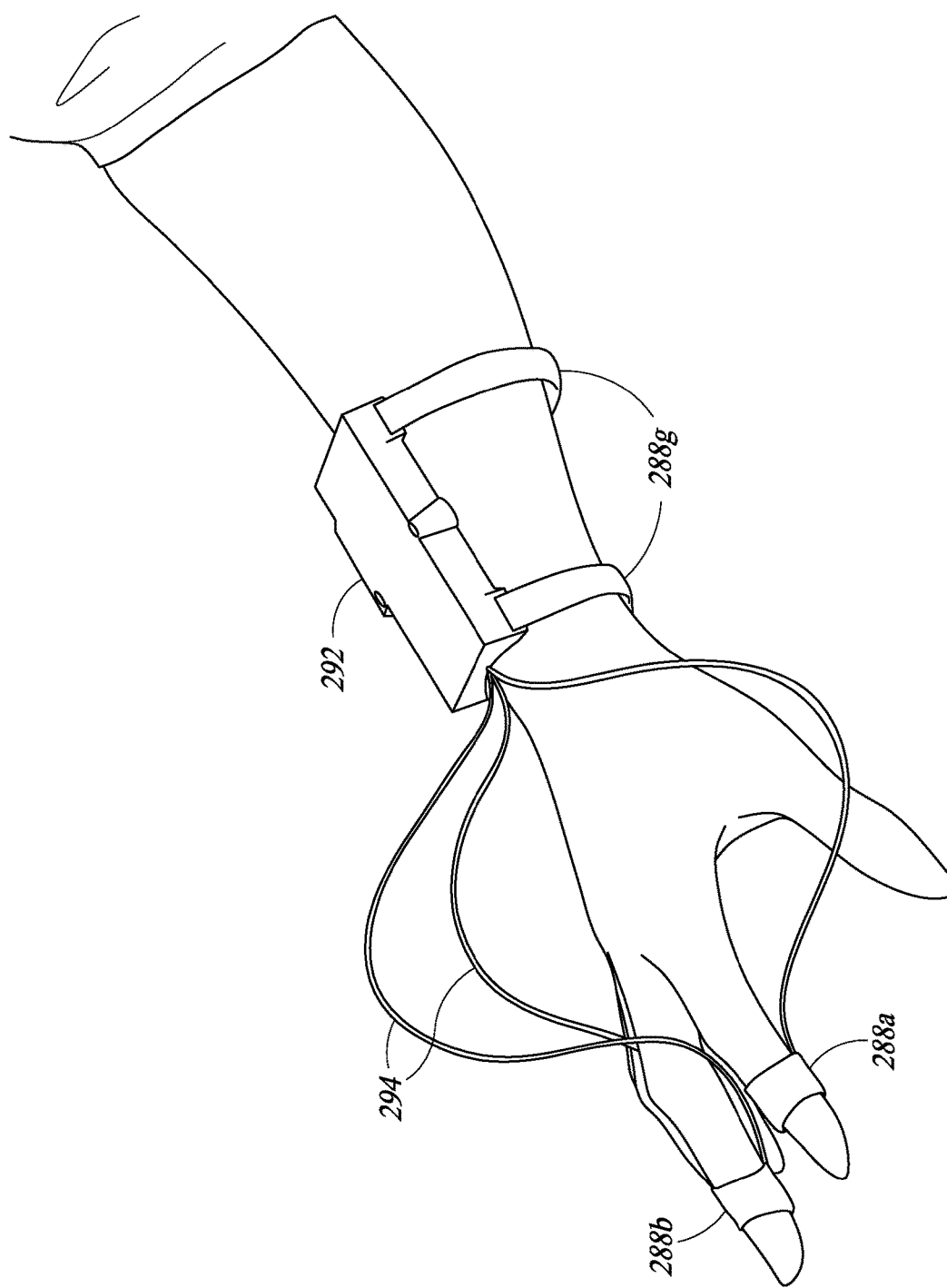
FIG. 2C is a side elevational view of the subject interface device of FIG. 2B shown mounted on the hand and arm of the individual, according to one illustrated implementation.

FIGS. 2A-2C show a subject interface device 222, according to one illustrated embodiment. The subject interface device 222 includes a number of components that are to be worn by a user, for example a practitioner 116 (FIG. 1). The subject interface device 222 of FIGS. 2A-2C may advantageously allow the practitioner 116 to feel the pulse, as well as electronically detect or measure the pulse.

In the illustrated embodiment, the subject interface device 222 can include three fingertip sensors or transducers 208a-208b (collectively 208) to detect pulse waveforms at three separate locations 286a, 286b, 286c along an artery, for example along the radial artery, the locations which may be closely spaced (i.e., within a thickness of an adult human finger) from one another along the artery. As previously noted, the fingertip sensors or transducers 208 may also be responsive to applied force or pressure. Alternatively, the subject interface device 222 can include one or more separate, dedicated sensors or transducers to detect or measure or produce a value proportional to applied force or pressure.

As best illustrated in FIGS. 2B and 2C, the subject interface device 222 includes one or more couplers 288a-288c that detachably physically couple the one or more sensors or transducers 208 to one or more fingers of the user (e.g., practitioner 116). The couplers may, for example, take the form of hook and loop material (e.g., VELCRO® 288a, 288b, 288c at joint of fingers, such as between middle and distal phalanx), tape, elastic bands (e.g., rubber or elastic bands), metal or plastic elastic clips (e.g., C-shaped clips), adhesive (e.g., adhesive pads 288d, 288e, 288f at fingertips), etc.

As illustrated in FIG. 2A, the subject interface device 222 may include one or more EKG leads 290a and sensors or transducers 290b. The EKG leads 290a and sensors or transducers 290b are detachably physically coupled to the subject, for example via an adhesive (not shown), for instance a pressure sensitive adhesive that is preferably a biocompatible adhesive.

In the illustrated embodiment, the subject interface device 122 can include electronics 224. The electronics may, for example, include an analog amplifier 226, ADC 228, and radio or wireless transmitter 230 (e.g., BLUETOOTH® transceiver, WI-FI® transceiver) and one or more antennas 232. The electronics 224 may be retained in a housing 292 that provides environmental protection.

The subject interface device 122 includes one or more couplers 288g (two shown in FIG. 2C) that detachably physically couple the electronics 224 and/or housing 292 to a forearm or other portion of the user. The couplers 288g may, for example, take the form of hook and loop material (e.g., VELCRO®), tape, elastic bands (e.g., rubber or elastic bands), metal or plastic elastic clips (e.g., C-shaped clips), belt, holster, adhesive, etc. Leads or electrically conductive wires 294, with appropriate insulation, communicatively coupled the sensors or transducers 208 to the electronics 224.

Figure 3A:
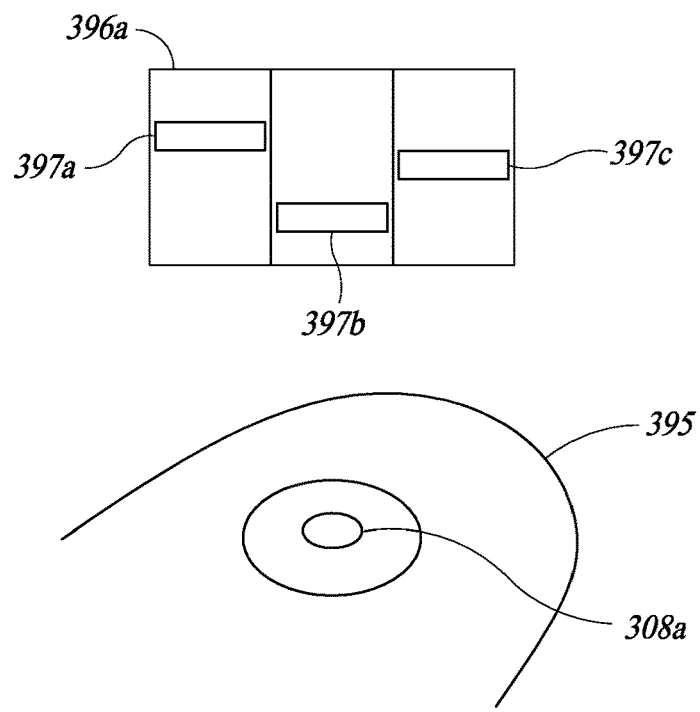
FIG. 3A shows a single sensor or transducer mounted on a fingertip, and a corresponding display of information discernable via use of the single sensor or transducer, according to one illustrated embodiment.

FIG. 3A shows a single sensor or transducer 308a mounted on a fingertip 395, and a corresponding display 396a of information discernable via use of the single sensor or transducer 308a, according to one illustrated embodiment.

Figure 4:
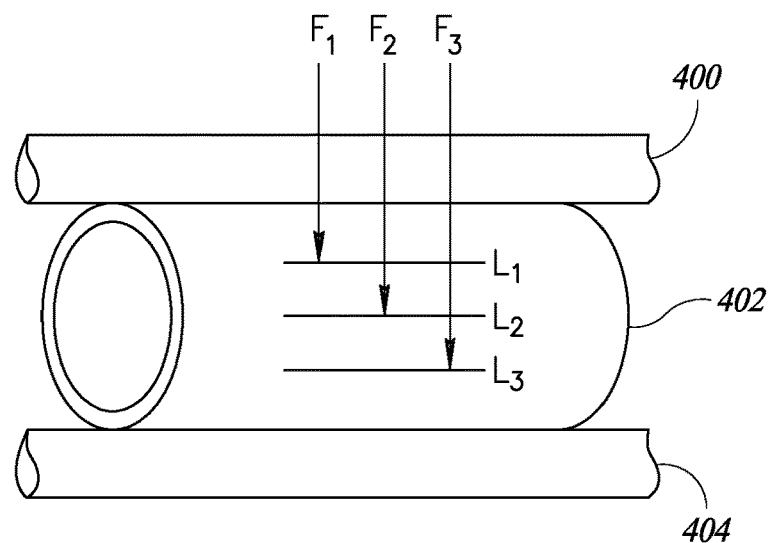
FIG. 4 is an isometric view of a portion of a body, for example a wrist, showing skin tissue, bone tissue, and an artery between the skin and bone tissue, and illustrating a plurality of levels of force or pressure, and consequent levels of depression of the skin tissue and artery, according to one illustrated embodiment.
Figure 5:
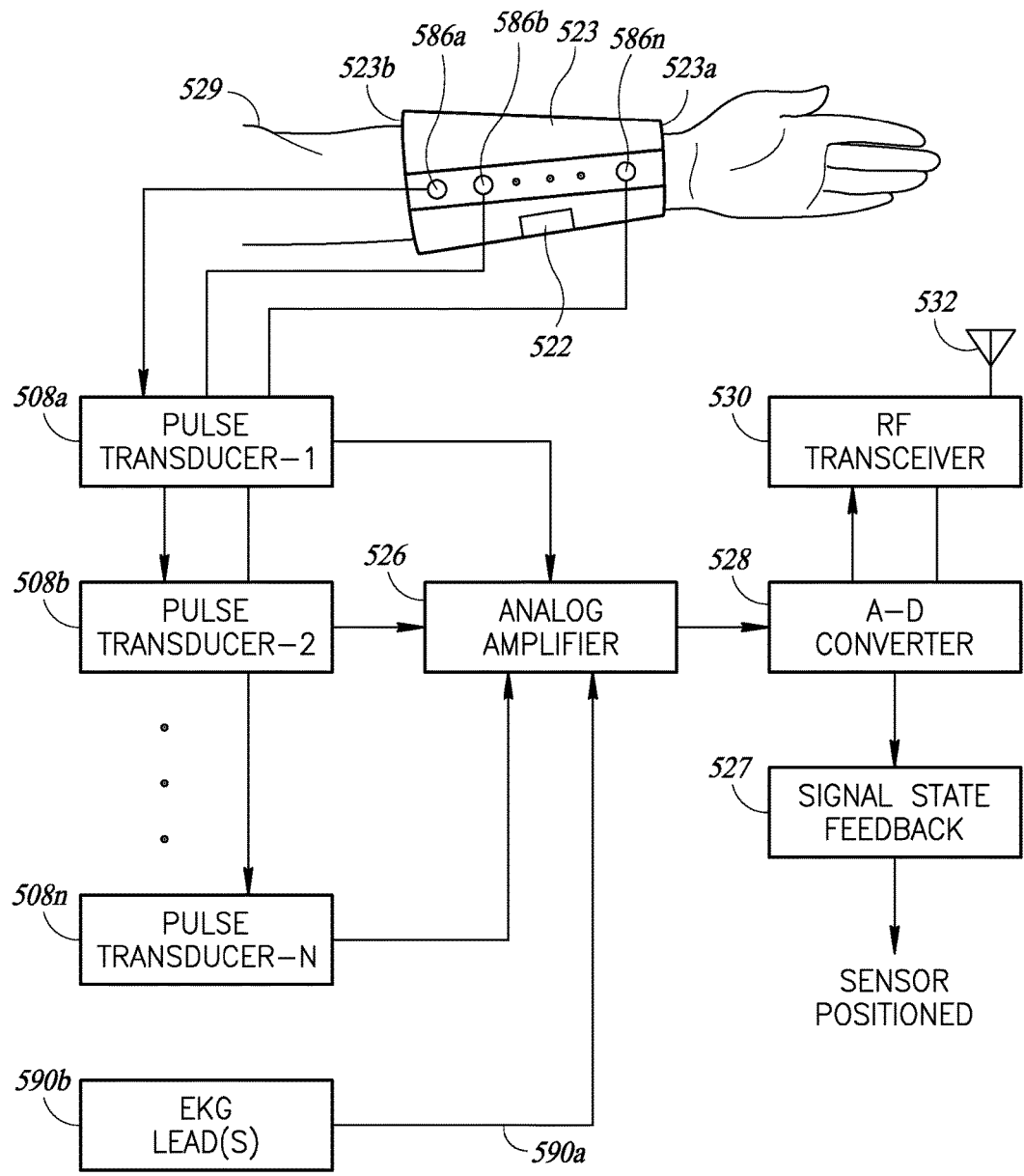
FIG. 5 is a schematic view of a subject interface device to capture pulse waveform signals from a subject, according to another illustrated implementation.

The single sensor or transducer 308a senses or detects a pulse at a single point, per fingertip 395. The sensor or transducer 308a may be applied to the subject 106 (FIG. 1) via skin 400 (FIG. 4) using one or more distinct levels of force $F_1$, $F_2$, $F_3$ (FIG. 4), for example three levels of force $L_1$, $L_2$, $L_3$ (FIG. 5), to press the sensor or transducer 308a into the skin 400 and artery 402 to three different levels of depth $L_1$, $L_2$, $L_3$ (FIG. 5). A first level of force $F_1$ may correspond to simply the weight of the sensor or transducer

308*a* without any force being exerted by the fingertip 395, and hence minimal depression of the skin 400 and artery 402 to the first depth level $L_1$. A second level of force $F_2$ may correspond to an intermediate level of force being applied via the fingertip 305, and hence an intermediate depth of depression of the skin 400 and artery 402 to the second depth level $L_2$. A third level of force $F_3$ may correspond to a relatively high level of force being applied via the fingertip 305, and hence a relatively deep depression of the skin 400 and artery 402 to a third depth level $L_3$. The high level of force $F_3$ may be sufficient to occlude the artery 402, for example pressing the radial artery 402 against a surface of a bone 404 (FIG. 4), e.g., the radius, sufficiently to occlude blood flow in the artery 402. Force or pressure may subsequently be slowly released, until pulsation returns in the subject area or volume. The second or intermediate level $F_2$, $L_2$ may, for example be midway between the first level $F_1$, $L_1$ and third level $F_3$, $L_3$ in both terms of force and terms of depression of the skin 400 and artery 402. Measurement of the pulse waveform may be delayed to account for the time required for the pulse to equalize after an initial in-rush of blood on releasing force or pressure immediately following applying the third level of force or pressure $F_3$.

A corresponding display 396*a* displays a depth 397 of maximum intensity of a pulse, which can visually represent a time history of pulse captured at each of one or more fingertips 396. The system can auto-correlate, cross-correlate and/or perform power spectral analysis on the collected or discerned information (e.g., time history of pulse captured at each of one or more fingertips). The system can, for example, determine, assess or characterize any one or more of blood viscosity, arterial stiffness or a pulse jerk (i.e., $3^{rd}$ derivative of pulse).

Figure 3B:
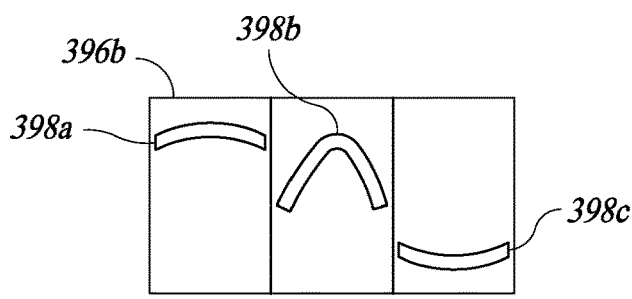
FIG. 3B shows a linear or one-dimensional array of sensors or transducers mounted on a fingertip, and a corresponding display of information discernable via use of the linear or one-dimensional array of sensors or transducers, according to one illustrated embodiment.
Figure 3B:
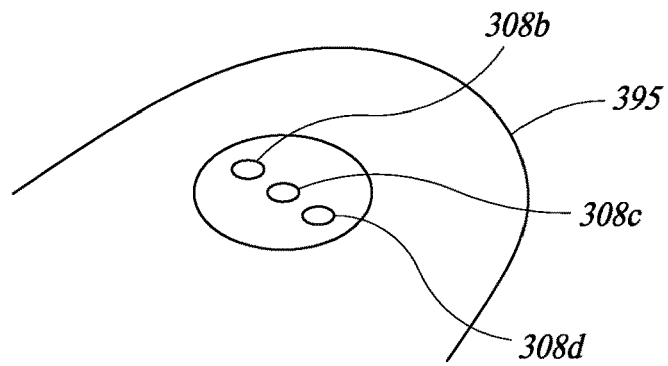

FIG. 3B shows a linear or one-dimensional array of sensors or transducers 308*b*, 308*c*, 308*d* mounted on a fingertip 395, and a corresponding display 396*b* of information discernable via use of the linear or one-dimensional array of sensors or transducers 308*a*-308*d*, according to one illustrated embodiment.

The linear or one-dimensional array of sensors or transducers 308*b*-308*d* sense or detect a pulse at multiple (e.g., three) points, per finger 395. The sensors or transducers 308*b*-308*d* may be applied to the subject using one or more distinct forces, for example three levels of force to press the sensor or transducer 308*a* into the skin and artery to three different levels of depth. Such is discussed above with reference to FIG. 3A, which discussion is not repeated in the interest of brevity.

A corresponding display displays a depth shape 398*a*, 398*b*, 398*c* (collectively 398) of the pulse. Such may allow higher resolution spatial analysis as compared to the single sensor or transducer (FIG. 3A). The sensors or transducers should be coaxially aligned with the artery during use. In addition to the characteristics detectable by the single sensor or transducer (FIG. 3A), information collected or discerned using the linear or one-dimensional array of sensors or transducers can, for example, allow the system to determine or assess or characterize blood pressure. Blood pressure waveform analysis can be accomplished via blind source separation, which can include, but is not limited to wavelet analysis, principal component analysis (PCA) and independent component analysis (ICA). PCA can, for example, utilize first and second moments of the measured data, hence relying heavily on Gaussian features. ICA can, for example, exploit inherently non-Gaussian features of the data and employs higher moments.

Figure 3C:
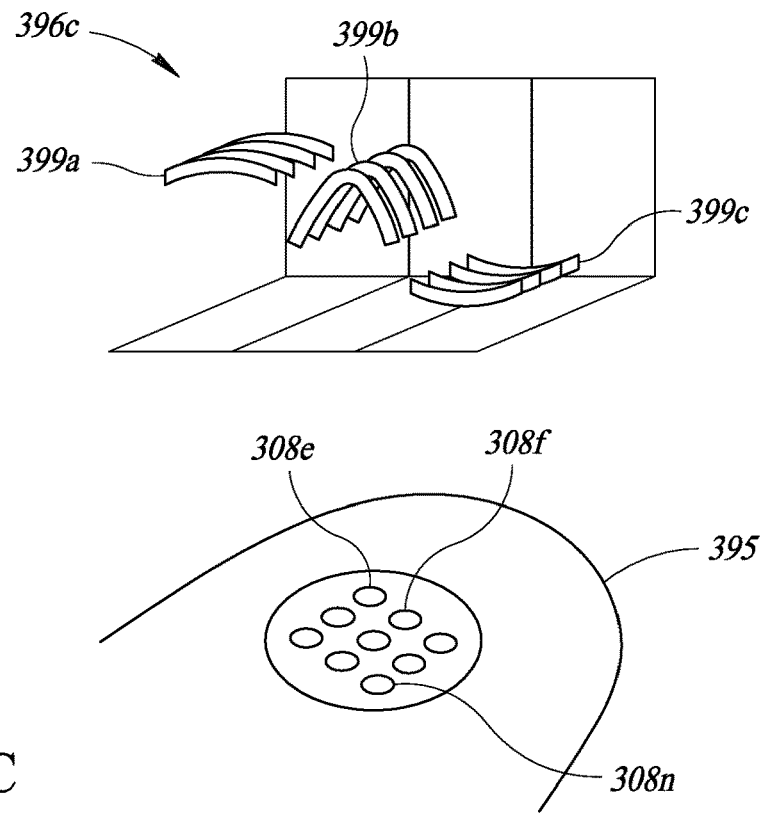
FIG. 3C shows a two-dimensional array of sensors or transducers mounted on a fingertip, and a corresponding display of information discernable via use of the two-dimensional array of sensors or transducers, according to one illustrated embodiment.

FIG. 3C shows a two-dimensional array of sensors or transducers 308*e*, 308*f*, . . . , 308*n* (nine shown, only 3 called out for drawing clarity) mounted on a fingertip 395, and a corresponding display 396*c* of information discernable via use of the two-dimensional array of sensors or transducers 308*e*-308*n*, according to one illustrated embodiment.

The two-dimensional array of sensors or transducers 308*e*-308*n* sense or detect a pulse at a two-dimensional array (e.g., nine) points, per finger 395. The sensors or transducers 308*e*-308*n* may be applied to the subject 106 (FIG. 1) using one or more distinct forces, for example three levels of force to press the sensor or transducer 308*a* into the skin and artery to three different levels of depth. Such is discussed above with reference to FIG. 3A, which discussion is not repeated in the interest of brevity.

A corresponding display displays a three-dimensional representation of the pulse 399*a*, 399*b*, 399*c* (collectively 399). Such may facilitate pulse finding. One of the primary dimensions of the array of sensors or transducers should be aligned with the artery during use. In addition to the characteristics detectable by the linear or one-dimensional array of sensors or transducers 308*b*-308*d* (FIG. 3B), the information collected or discerned via the two-dimensional array of sensors or transducers can, for example, allow the system to determine or assess or characterize arterial morphology.

FIG. 5 shows a subject interface device 522, according to one illustrated embodiment. The subject interface device 522 includes a number of components that are carried by a sleeve or cuff which is designed to be worn by a user, for example a subject 106 (FIG. 1). Use of a subject worn sleeve or cuff can advantageously avoid the introduction of noise by the practitioner, for example avoiding detection of the practitioner's own pulse, which could possible occur with a practitioner worn subject interface device (e.g., FIG. 2.)

In the illustrated embodiment, the subject interface device 522 can include three sensors or transducers 508*a*, 508*b*-508*n* (collectively 508) to detect pulse waveforms at a plurality of separate locations 586*a*-586*n* along an artery, for example along the radial artery, the locations which may be closely spaced (i.e., within a thickness of an adult human finger) from one another along the artery. As previously noted, the sensors or transducers 508 may also be responsive to applied force or pressure. Alternatively, the subject interface device 522 can include one or more separate, dedicated sensors or transducers to detect or measure or produce a value proportional to applied force or pressure.

In the illustrated embodiment, the subject interface device 522 can include electronics, for example enclosed in a housing 522. The electronics may, for example, include an analog amplifier 526, ADC 528, and radio or wireless transmitter 530 (e.g., BLUETOOTH® transceiver, WI-FI® transceiver) and one or more antennas 532. The electronics can optionally include one or more position or orientation sensors or transducers 527, or other component that produces position information indicative of at least a position and/or orientation of at least the sensors or transducers 508 and possibly the entire subject interface device 522. Such can allow determination of whether the sensors or transducers 508 are properly positioned and aligned with the artery. The electronics can include one or more accelerometers (e.g., three-axis accelerometers) and/or one or more optical LED and photodetector pairs. For example, a respective accelerometer or optical LED and photodetector pair can be associated with each of the sensors or transducers. Such can allow the electronics to subtract movement from adjacent sensors or transducers from a sensor or transducer that detects the largest pulse waveform pressure. The electronics can be retained in the housing 522 which provides environmental protection.

Figure 7:
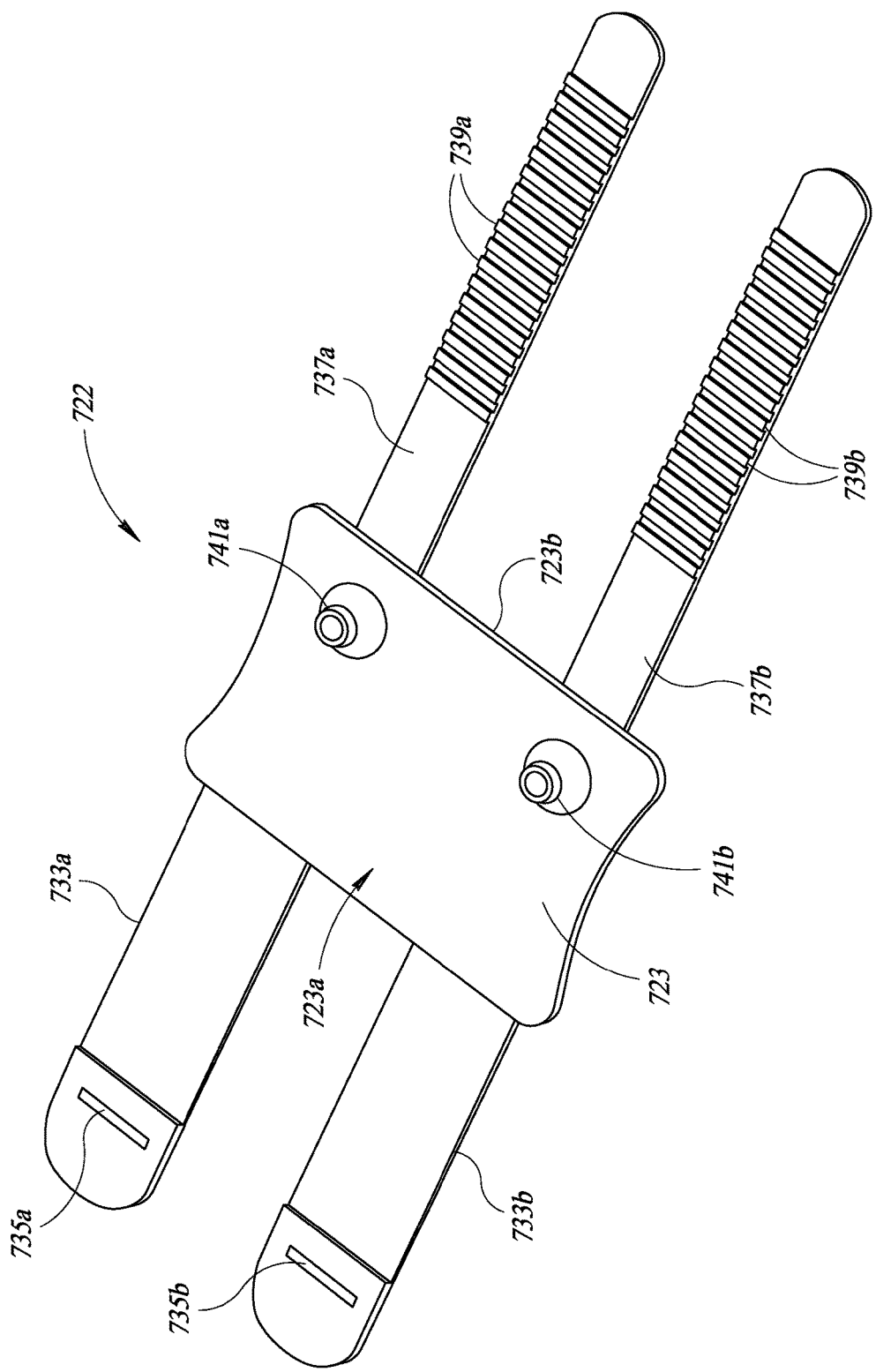
FIG. 7 is a schematic view of a subject interface device to capture pulse waveform signals from a subject, according to yet another illustrated implementation.

The subject interface device 522 includes a sleeve or cuff 523 that detachably physically couples the one or more sensors or transducers and electronics to a portion of an arm 529 of the user (e.g., subject 106). The sleeve or cuff 523 may, for example, take a generally tubular form, and may or may not taper in diameter from one end to another. The sleeve or cuff 523 may be a closed, integral or unitary piece of material, having only a pair of opposed openings, one at each end 523a, 523b, and which can only be mounted on the arm 529 by passing the arm 529 first though one opening and then through the other opening. Alternatively, the sleeve or cuff 523 may be a piece of material that can be wrapped around the arm 529 (e.g., forearm, wrist), and then closed by drawing two opposing sides together and fastening with a coupler, for example as illustrated in FIG. 7. Suitable couplers may include hook and loop material (e.g., VELCRO®), tape, belt and buckles, snap fasters, metal or plastic elastic clips, slot and beveled teeth or ridges (e.g., FIG. 7), adhesive, etc. In either case, the material can, for example, be an elastic material (e.g., rubber) to securely retain the sleeve or cuff 523 in position during use. Alternatively, one or more bands (e.g., rubber or elastic bands), or metal or plastic clips (e.g., C-shaped clips) can be used to secure the sleeve or cuff 523 in position during use.

As illustrated in FIG. 5, the subject interface device 522 may include or be associated with one or more EKG leads 590a and sensors or transducers 590b. The EKG leads 590a and sensors or transducers 590b are detachably physically coupled to the subject 106 (FIG. 1), for example via an adhesive, for instance a pressure sensitive adhesive that is preferably a biocompatible adhesive.

In some implementations, two sleeve or cuff 523 subject interface devices 522 can be concurrently employed on a single subject. Such can allow for single trace EKG/ECG signal collection. A serial data link can be established through the skin or body of the subject between the EKG/ECG measurements. Such can take the form of an ultralow power device, for example charged by kinetic energy and/or solar energy, at least one the EKG/ECG side.

Figure 6:
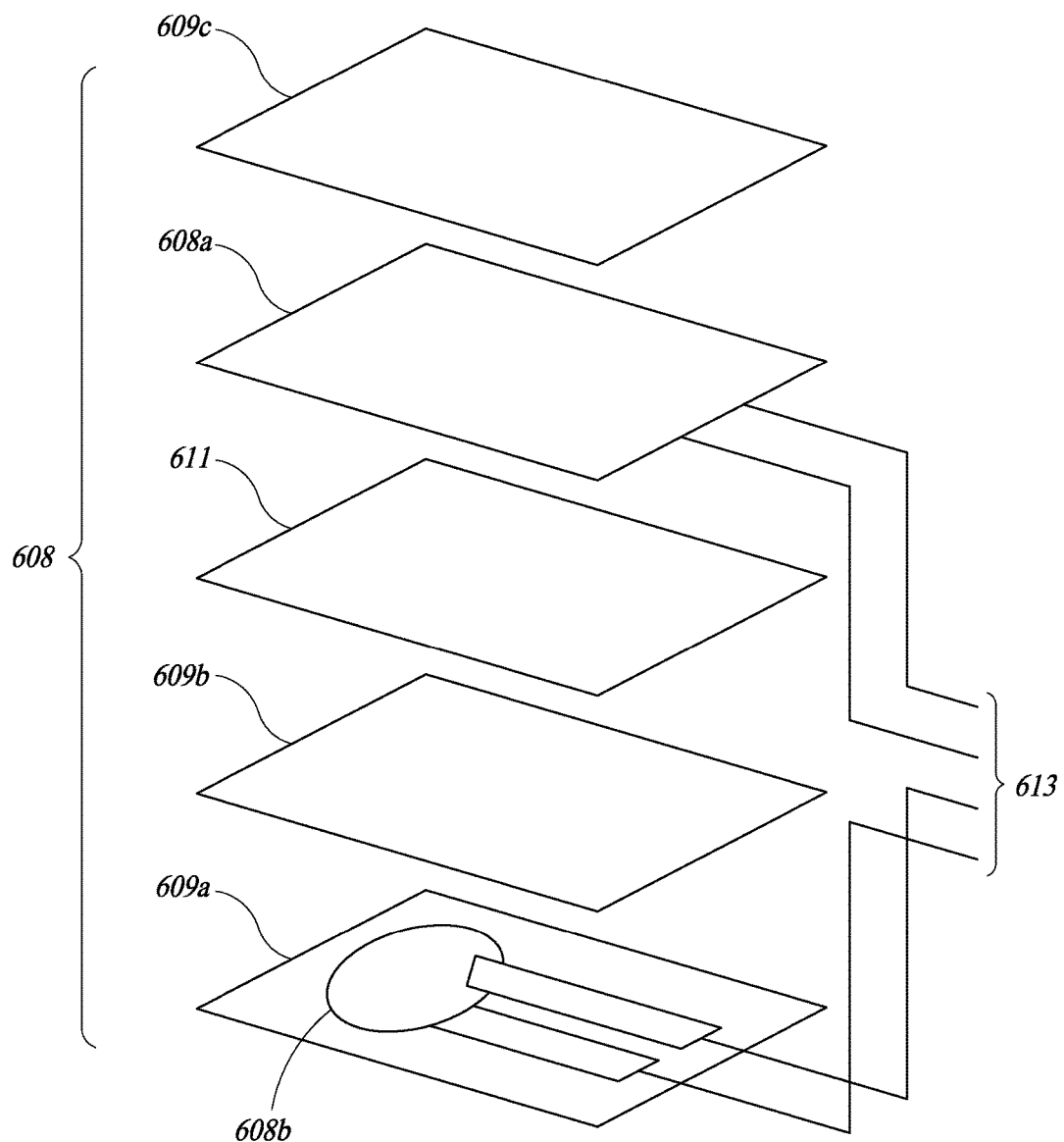
FIG. 6 shows a combined sensor or transducer structure that includes a pulse waveform responsive sensor or transducer and an applied force responsive sensor or transducer, formed together, according to one illustrated embodiment.

FIG. 6 shows a combined sensor or transducer structure 608 that is responsive to a pulse waveform and responsive to an applied force, to produce signals indicative of a pulse waveform and indicative of an applied force, according to one illustrated embodiment.

The combined sensor or transducer structure 608 includes a first sensor or transducer 608a which is responsive to a pulse waveform in an artery that is detected through skin. The first sensor or transducer 608a can, for example, take the form of a piezoelectric film or substrate as illustrated in FIG. 6. The combined sensor or transducer structure 608 includes a second sensor or transducer 608b which is responsive to applied force or pressure asserted on the skin and artery via the combined sensor or transducer structure 608. The second sensor or transducer 608b can, for example, take the form of a force sensitive resistor as illustrated in FIG. 6. The second sensor or transducer 608b can, for example, be coupled to a Wheatstone bridge or other circuit (not shown) to determine a voltage across the force sensitive resistor 608b, and produce a corresponding signal which is proportional to force.

The combined sensor or transducer structure 608 may include a first electrically insulative substrate 609a, for example a MYLAR® film or substrate, on which the second sensor or transducer 608b (e.g., force sensitive resistor) is carried. The combined sensor or transducer structure 608 may include a second electrically insulative substrate 609b, for example a MYLAR® film or substrate, between the first sensor or transducer 608a (e.g., piezoelectric film or substrate) and the second sensor or transducer 608b (e.g., force sensitive resistor). The combined sensor or transducer structure 608 may include an adhesive 611 (e.g., adhesive layer) between the second electrically insulative substrate 609b and the first sensor or transducer 608a (e.g., piezoelectric film or substrate). The combined sensor or transducer structure 608 may further include a third electrically insulative substrate 609c, that overlies and protects the first sensor or transducer 608a (e.g., piezoelectric film or substrate). One or more wires, conductive traces or other conductive structures 613 can lead from the first and second sensors or transducers 608a, 608b, to communicatively couple such to one or more amplifiers and/or ADCs.

The combined sensor or transducer structure 608 advantageously aligns or places the first and the second sensors or transducers in registration with one another, ensuring accurate reading of applied forces relative to sensed pulse waveform. The combined sensor or transducer structure 608 also provides a compact package and economical design. The combined sensor or transducer structure 608 may advantageously be used in any of the previously described implementations or embodiments, or in the implementations or embodiments described below.

FIG. 7 shows a subject interface device 722, according to one illustrated embodiment. The subject interface device 722 includes a number of components that are carried by a sleeve or cuff 723 which is designed to be worn by a user, for example a subject 106 (FIG. 1).

The subject interface device 722 can include one, and preferably more, sensors or transducers (not visible in FIG. 7) to detect pulse waveforms at a plurality of separate locations along an artery, for example along the radial artery, the locations which may be closely spaced (i.e., within a thickness of an adult human finger) from one another along the artery. As previously noted, the sensors or transducers may also be responsive to applied force or pressure, for instance the combined sensor or transducer structure 608 illustrated in, and described with reference to, FIG. 6. Likewise, the subject interface device 722 can include electronics (not shown in FIG. 7), for example enclosed in a housing (not shown in FIG. 7). The electronics and/or housing can take the form of any of the previously described electronics and housing. The sensors or transducers and/or electronics and/or housing may be integrated in the sleeve or cuff 723, with only the sensors or transducers exposed, for example on an inside surface of the sleeve or cuff 723 when worn on the arm.

The subject interface device 722 includes a sleeve or cuff 723 that detachably physically couples the one or more sensors or transducers and electronics to a portion of an arm of the user (e.g., subject 106). The sleeve or cuff 723 may, for example, take a generally tubular form in use, and may or may not taper in diameter from one end to another. The sleeve or cuff 723 may be a piece of material that can be wrapped around the arm (e.g., forearm, wrist), and then closed by drawing two opposing sides 723a, 723b toward one another and fastening with a coupler. Suitable couplers may include straps 733a, 733b with slots 735a, 735b and complementary straps 737a, 737b with teeth 739a, 739b (e.g., beveled teeth or ridges), hook and loop material (e.g., VELCRO®), tape, belt and buckles, snap fasters, metal or plastic elastic clips, adhesive, etc. In either case, the material can, for example, be an elastic material (e.g., rubber) to securely retain the sleeve or cuff in position during use. For example, the sleeve or cuff 723 can be 3D printed from a material, for instance thermoplastic elastomers (TPE) for 3D printing commercially available from Ninjaflex. Alternatively, one or more separate and distinct bands (e.g., rubber or elastic bands), or metal or plastic clips (e.g., C-shaped clips) can be used to secure the sleeve or cuff 723 in position during use.

The sleeve or cuff 723 advantageously forms one or more bladders having an interior or chamber that holds a fluid (e.g., gas, air). The sleeve or cuff 723 advantageously includes two or more ports 741a, 741b that provide fluid communication with the interior or chamber of the bladder. A source of air or other fluid can be coupled to the ports 741a, 741b to adjust a pressure in the bladder. In particular, the ports 741a, 741b can be used to create and/or control a differential pressure along a portion of a length of an artery by differentially inflating bladders while detecting pulse pressure waveforms. Such advantageously facilitates blood pressure readings without occlusion of the artery.

Figure 8:
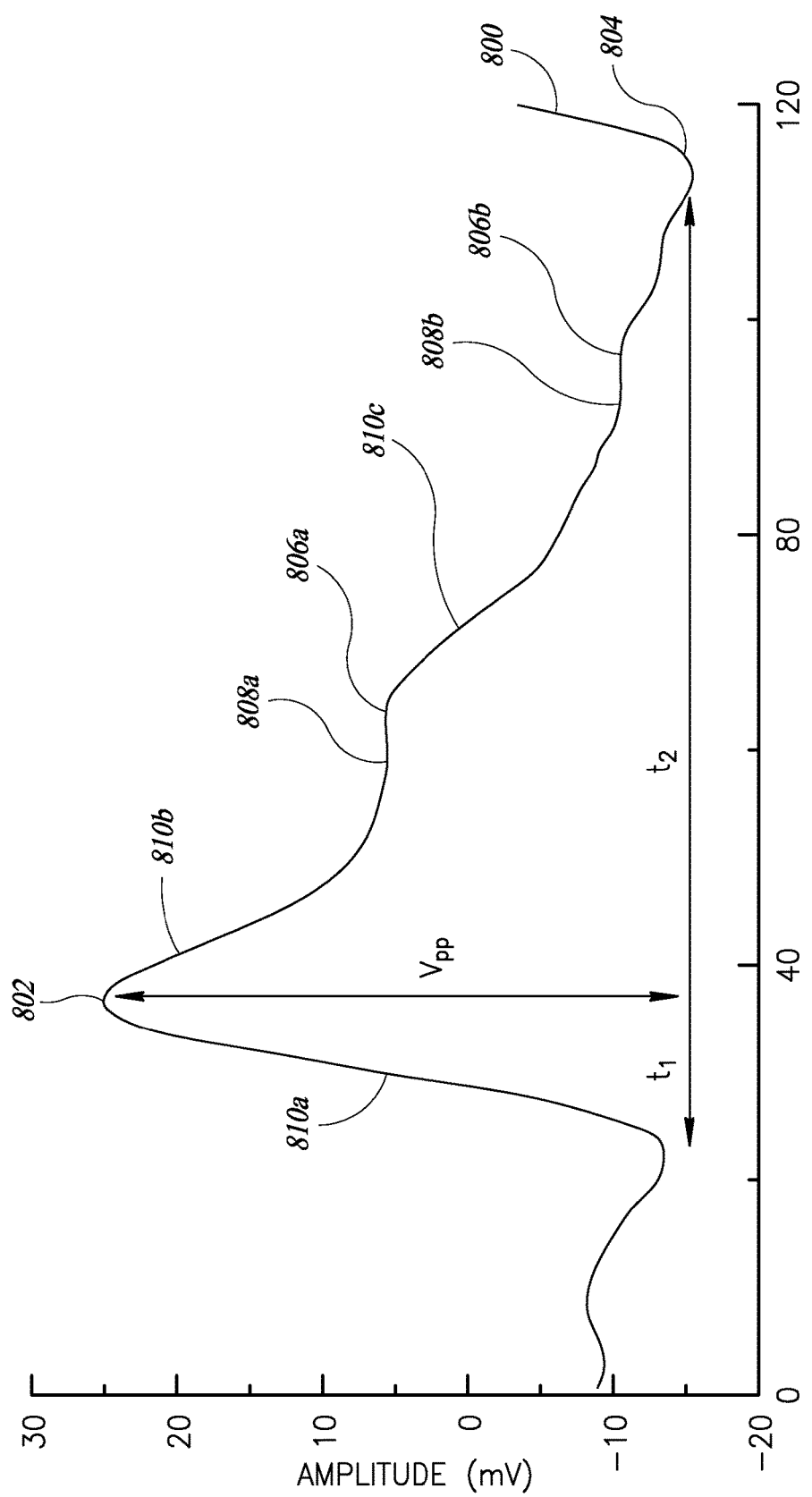
FIG. 8 is a graph showing an exemplary pulse waveform with defining characteristics or features, according to another illustrated implementation.

FIG. 8 shows a pulse waveform 800 according to one illustrated embodiment.

The pulse waveform 800 may be represented in a variety of fashions, for example pressure versus time, or amplitude (e.g., millivolts) versus samples.

The pulse waveform 800 has a variety of defining characteristics and features, which are useful in assessing health and wellness, and in generating diagnoses and/or remedial or preventive measures and/or generating metrics of cardiac function.

According to some traditional medicine systems, each pulse consists of four parts, i) an expansion, followed by ii) a pause, then iii) a contraction followed by iv) a second pause. Some traditional medicine systems employ ten criteria to evaluate a pulse: size, fastness or slowness, strength or weakness, shortness or length of pulse intervals, softness or hardness, similarity or dissimilarity, regularity or irregularity in diverse pulses and harmony related to musical nature of the pulse.

The pulse waveform 800 may include a global maxima 802 and global minima. The pulse waveform 800 may include one or more local maxima 806a, 806b and/or local minima 808a, 808b. The pulse waveform 800 may also include various slopes or gradients 810a, 810b, 810c between the various global and local maxima 802, 806a, 806b and global and local minima 804, 808a, 808b. The pulse waveform 800 may also include various times or frequency between various pairs of the other defining characteristics or features. While the signal analysis herein is generally discussed in terms of time domain signal analysis techniques, the system 100 can employ frequency domain signal analysis techniques.

Various techniques, for example machine-learning techniques, can be employed for identifying which defining characteristics and features of the pulse waveform 800 are medically significant, the significance of those defining characteristics and features, and the corresponding diagnoses and/or remedial or preventive measures that correspond to those defining characteristics and features and/or the corresponding metrics of cardiac function.

Figure 9:
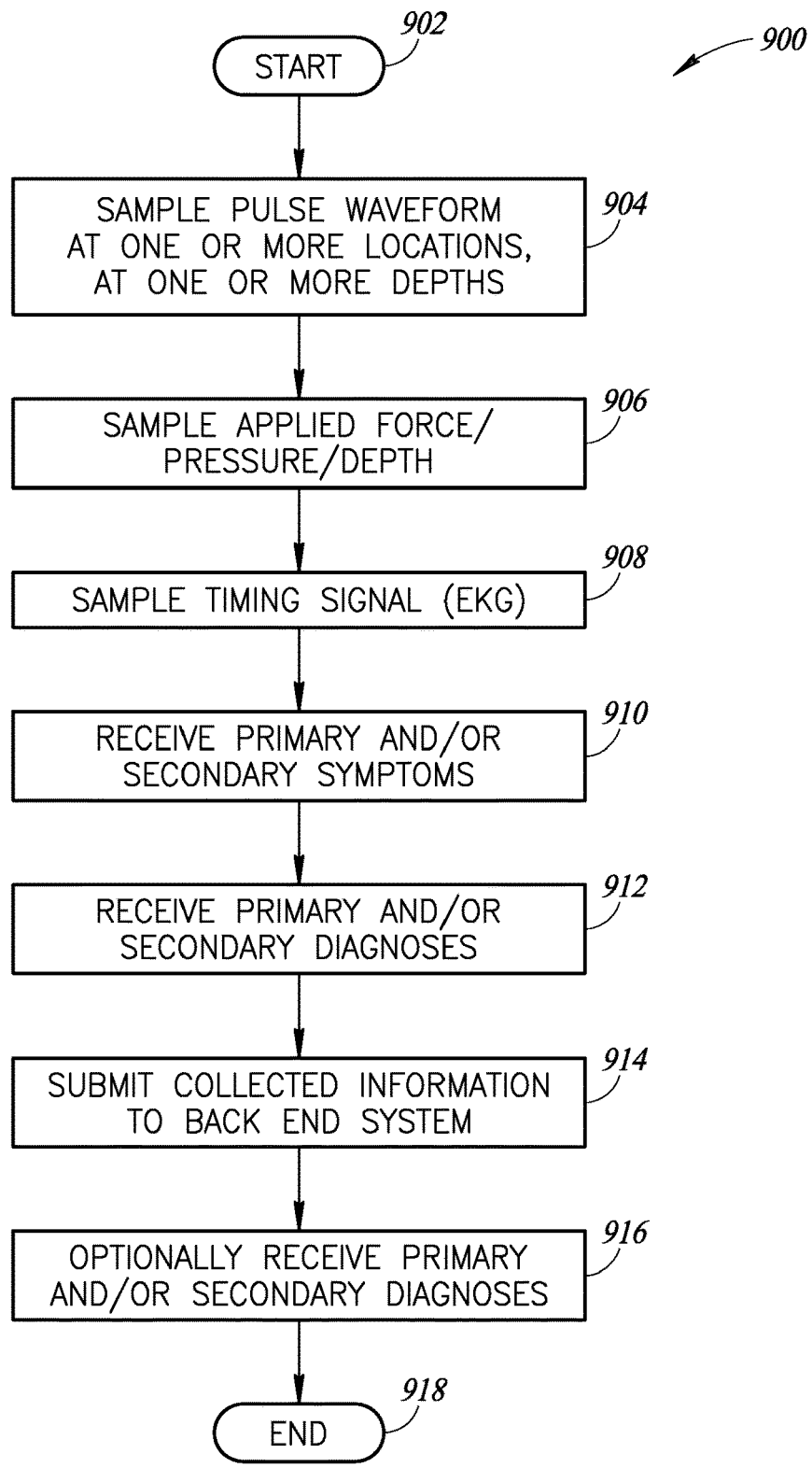
FIG. 9 is a flow diagram of a method of operation in a diagnostic system, for example a front-end system to collect diagnostically relevant information for a number of subjects, according to one illustrated implementation.

FIG. 9 shows a method 900 of operation in a diagnostic system, according to at least one illustrated embodiment. The method 900 can be implemented by a front-end system, similar or even identical to that illustrated and described with respect to FIG. 1.

The method 900 starts at 902. For example, the method 900 may start on application of power to the front-end system or portion thereof. Alternatively, the method 900 may start on uses of a user interface device and/or user input system by a practitioner, such as those illustrated in FIG. 1. As a further alternative the method 900 may start in response to being invoked by a calling program, routine or subroutine. While described in terms of one subject, the method 900 may be employed with a large number of subjects, and by a large number of practitioners, which may advantageously improve the reliability of the system to the extent such relies on machine-learning techniques.

At 904, a user interface device samples pulse waveforms at one or more locations (e.g., three sensors at three locations), and at one or more depths (e.g., three depths) at each location. Thus, each sensor or transducer can collect or capture pulse waveforms at each of two or more depths (i.e., two or more levels of force or pressure).

At 906, the user interface device samples applied force, pressure and/or depth at which the pulse waveforms are being sampled. Thus, one or more sensors or transducers can collect or capture signals that are proportional to applied force, pressure or depth.

At 908, the user interface device samples or discerns one or more timing signals. As described elsewhere herein, one or more EKG sensors or terminals may be positioned to detect electrical activity of a heart of the subject. Such provides a clear indication of a contraction, and hence a start of a blood pulse cycle. A knowledge of the delay or time it takes for a blood pulse to reach the area being monitored (e.g., radial artery proximate wrist), allows the timing information to be used to better discern signal (e.g., pulse) out of noise (e.g., subject or practitioner movement, electrical noise).

At 910, a user interface system receives one or more primary symptoms and/or secondary symptoms. Such may be entered by the practitioner, or alternatively by the subject, in a variety of ways. Such can be entered via a user interface, for instance a graphical user interface. Such can include typing on a keyboard, for example into one or more freeform text entry fields. Such can include selecting from a pull-down menu or list, or other user interface structure. The symptoms may be reported by the subject and/or may be observed by the practitioner. Symptoms can, for example, include pain in certain body parts, shortness of breath, fatigue, fever, aches, etc.

At 912, a user interface system receives one or more primary diagnoses and optionally one or more secondary diagnoses. Such may be entered by the practitioner, or alternatively by the subject, in a variety of ways. Such can be entered via a user interface, for instance a graphical user interface. Such can include typing on a keyboard, for example into one or more freeform text entry fields. Such can include selecting from a pull-down menu or list, or other user interface structure. The diagnosis is typically a learned conclusion by the practitioner based on various factors such as familiarity with the pulse waveforms and symptoms. Diagnosis can take many forms, including specific medical conditions or syndromes. Such may additionally include specification of suggested remedial or preventive measures and/or metrics of cardiac function.

At 914, the front-end system submits the collected information to a back-end system, for example the back-end system illustrated in FIG. 1. The front-end system or a component thereof, can compile the information (e.g., pulse wave information, timing information, symptom specifying information, diagnoses information) for sending to the back-end as a packet, or in manner that the back-end system can draw a logical relation between the various pieces of information. For example, the information can all be logically associated via a shared unique identifier that is unique to the particular patient/subject visit and practitioner. In some instances, the information may be transmitted without any information that would uniquely identify the particular patient (i.e., anonymized), which can be particular useful when initially preparing a dataset for machine learning. As noted elsewhere, the front-end system can employ any known method of communications to transmit the collected information to the back-end system.

Optionally at 916, the front-end system receives one or more system generated primary diagnoses and/or one or more system generated secondary diagnoses. In some instances, collected information may be transmitted only for the purpose of populating a database or dataset. In such instances, the collected information will typically include the practitioner's own diagnoses. Thus, in such instances there may be no reason to return any system generated diagnoses. In other instances, a practitioner may not have a diagnoses, or may want to have their diagnosis confirmed against a system generated diagnosis.

The method 900 ends at 918. In some implementations, the method 900 may repeat continuously or periodically. The method 900 may be run in multiple instances in parallel, for example as many threads operating on one or more processors.

Figure 10:
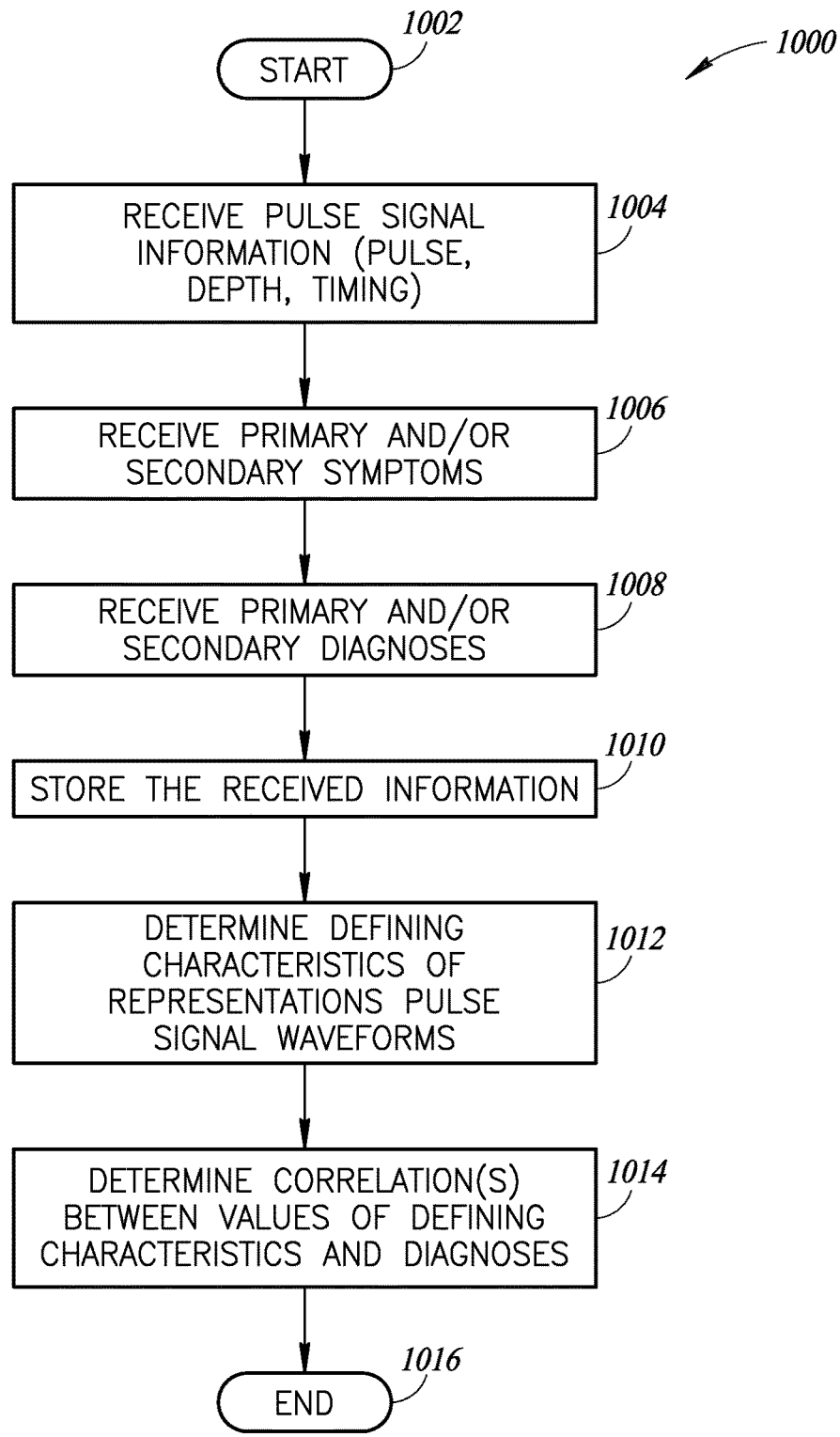
FIG. 10 is a flow diagram of a method of operation in a diagnostic system, for example a back-end system to process diagnostically relevant information for a number of subjects, for example via machine-learning techniques, according to one illustrated implementation.

FIG. 10 shows a method 1000 of operation in a diagnostic environment, according to at least one illustrated embodiment. The method 1000 can be implemented by a back-end system, similar or even identical to that illustrated and described with respect to FIG. 1.

The method 1000 starts at 1002. For example, the method 1000 may start on application of power to the back-end system or portion thereof. Alternatively, the method 1000 may start on receipt of an inquiry or request by, or submission of collected information from, a front-end system. As a further alternative the method 1000 may start in response to being invoked by a calling program, routine or subroutine. While described in terms of one subject, the method 1000 may be employed with a large number of subjects, and by a large number of practitioners, which may advantageously improve the reliability of the system to the extent such relies on machine-learning techniques.

At 1004, the back-end system receives pulse signal information from one of the front-end systems. The pulse signal information can take a variety of forms.

The pulse signal information can include representations of one or more pulse waveforms sampled from one or more locations along an artery, at one or more levels of applied force, hence depth of depression of the skin and artery. The pulse signal information can take the form of analog pulse waveforms, digitized pulse waveforms, and/or information that characterizes the pulse waveforms, for instance values for one or more defining characteristics or defining features of the pulse waveforms.

The pulse signal information can also include information that specifies a level of applied force, pressure or depth (deformation of skin or tissue) for each of the pulse waveform representations or data.

The pulse signal information can also include information that specifies timing information for one, more or preferably all of the pulse waveform representations or data. The back-end system can employ the timing information to better discern the various defining characteristics or features of the pulse waveform from any potential noise in the pulse waveform representations. In some implementations, the front-end system may employ the timing information in preprocessing the pulse waveforms, thus it may not be necessary that the back-end system receive the timing information. The back-end system employs the pulse waveforms and the force, pressure or depth information to determine or generate system generated diagnosis, either with or without the symptoms information. The force, pressure or depth information is particularly relevant to creating various reflections in the vasculature, allowing the back-end system to employ a form of reflectometry in analysis of the pulse waveforms. For example, in some implementations, the system can average a subtraction of an average of previous pulse waveforms from a current pulse waveform to detect reflections occurring during a main pulse event. This can allow the system to detect and characterize reflections that would otherwise be hidden inside the current or next pulse cycle. While the signal analysis herein is generally discussed in terms of time domain signal analysis techniques, the system 100 can employ frequency domain signal analysis techniques.

At 1006, the back-end system receives one or more primary symptoms and/or secondary symptoms from the front-end systems. The primary symptoms and/or secondary symptoms are symptoms that a given subject has experienced or is experiencing, or which a practitioner has observed in the given subject from whom the pulse waveform information was generated. In some implementations, the back-end system will take into account a subject's symptoms in addition to or as part of assessing pulse waveforms and generating one or more system generated primary or secondary diagnoses. A primary symptom can be a symptom that is more likely relevant to diagnosing a condition, ailment or malady, while a secondary symptom may be one deemed less likely relevant or one that is common to a large number of conditions, ailments or maladies.

At 1008, the back-end system receives one or more primary diagnoses and/or one or more secondary diagnoses. The primary diagnoses and/or secondary diagnoses are diagnoses that are provided by a practitioner who is examining a subject. In some instances, the primary and/or secondary diagnoses can be conclusions reached by a practitioner, and which the practitioner is submitting to help form a database or dataset of information. In some instances, the primary and/or secondary diagnoses can be preliminary conclusions reached by a practitioner, and which the practitioner is submitting for validation against system generated primary and/or secondary diagnoses, or against a database or dataset that is generated from a large population of subjects and practitioners, and hence a large population of pulse waveforms and conditions, ailments or maladies. In yet other instances, the primary and/or secondary diagnoses can be conclusions reached by a practitioner as part of training, and which the practitioner is submitting for validation against system generated primary and/or secondary diagnoses. In some implementations, the back-end system will take into account a practitioner's primary and/or secondary diagnoses for a given subject in addition to or as part of assessing pulse waveforms and/or symptoms in generating one or more system generated primary or secondary diagnoses.

While described as separate acts, the back-end system can concurrently receive the pulse signal information, the one or more primary symptoms and/or secondary symptoms, and/or the one or more primary diagnoses and/or one or more secondary diagnoses for a given subject. In some implementations, all of the collected information can be packaged and sent as a unit. Such information may or may not include subject specific identification information, for example name, address, social security number or other unique identifying information. Such information may or may not include non-subject specific information, for instance subject demographic information, for example age or age range, gender, race or ethnicity, smoker status, etc. Such information may or may not include non-subject specific information, for instance subject medical history.

At 1010, the back-end system stores the received information. For example, a runtime system may store the received information to a database, dataset or other data structure in or on one or more nontransitory computer- or processor-readable media.

At 1012, the back-end system determines or identifies defining characteristics or features of the representations of the pulse signal waveforms. As described above, the pulse waveforms may have various defining characteristics or features, for example global maxima, global minima, local maxima, local minima, slopes or gradients, or time or frequency between various pairs of the other defining characteristics or features. As described elsewhere herein, the back-end system may employ any of a variety of machine-learning techniques to determine or identify the defining characteristics or features of the representations of the pulse signal waveforms.

At 1014, the back-end system determines or identifies one or more correlations between various values of the defining characteristics or feature and the one or more diagnoses. As described elsewhere herein, the back-end system may employ any of a variety of machine-learning techniques to determine or identify one or more correlations between various values of the defining characteristics or features and the one or more diagnoses.

The method 1000 ends at 1016. In some implementations, the method 1000 may repeat continuously or periodically. The method 1000 may be run in multiple instances in parallel, for example as many threads operating on one or more processors.

Figure 11:
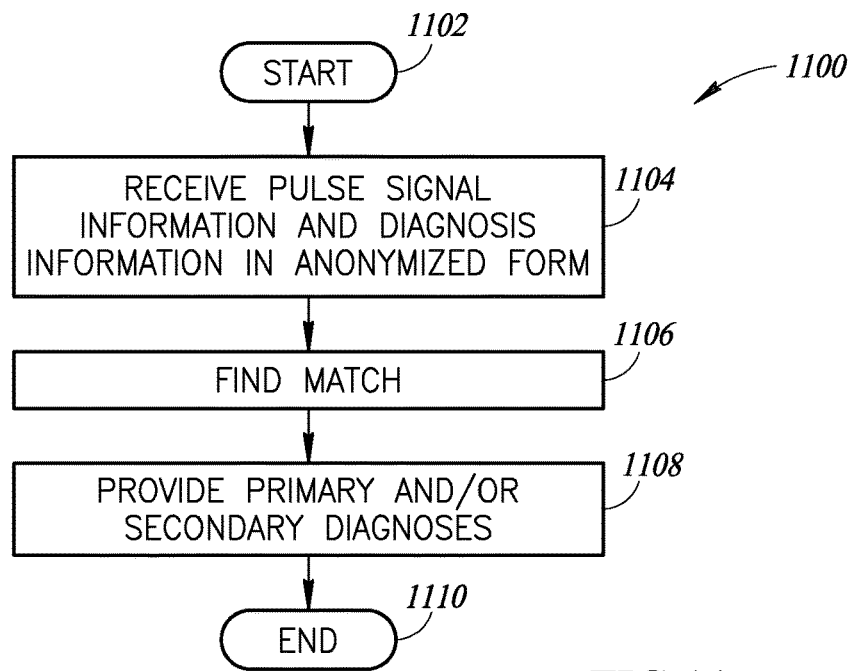
FIG. 11 is a flow diagram of a method of operation in a diagnostic system, for example a runtime system of a back-end system to process diagnostically relevant information for a number of subjects, according to one illustrated implementation.

FIG. 11 shows a method 1100 of operation in a diagnostic environment, according to at least one illustrated embodiment. The method 1100 can be implemented by a back-end system, similar or even identical to that illustrated and described with respect to FIG. 1. For example, the method 1100 can be executed by a runtime system, for example using a machine-learning generated dataset.

The method 1100 starts at 1102. For example, the method 1100 may start on application of power to the back-end system or portion thereof (e.g., runtime system). Alternatively, the method 1100 may start on receipt of an inquiry or request by, or submission of collected information from, a front-end system. As a further alternative the method 1100 may start in response to being invoked by a calling program, routine or subroutine. While described in terms of one subject, the method 1100 may be employed with a large number of subjects, and by a large number of practitioners, which may advantageously improve the reliability of the system to the extent such relies on machine-learning techniques.

At 1104, the back-end system receives pulse signal information and diagnosis information in anonymized form. Thus, the received information cannot be related back to a particular subject from which the received information was discerned, except possibly by a practitioner who submitted the anonymized information. In some implementations, even the practitioner who submitted the anonymized information cannot related the submitted information back to a particular subject.

At 1106, the back-end system finds one or more matches for the anonymized information. For example, the back-end system may employ any of a variety of matching algorithms against a database, dataset or other data structure. Also for example, the back-end system can employ a machine-learning system and/or data set to find one or more matches. The back-end system may look for exact matches. Alternatively or additionally, the back-end system can look for loose matches, that is matches where some subset of a set of constraints are satisfied or where some constraints themselves are loosely satisfied (i.e., value of constraint does not exactly match the target value, but is within some acceptable range of the target value).

At 1108, the back-end system generates and/or provides one or more primary diagnoses and/or secondary diagnoses based on the matching. For example, the back-end system may find a large number or percentage of matches to certain constraints or criteria, and employ diagnoses that map or correspond to those matches. For instance, the back-end system may find numerous instances of other subjects with identical or similar pulse waveforms for the given locations and/or applied forces or pressures. The back-end system can generate one or more primary and/or secondary diagnoses based at least in part on a consensus of practitioner assigned or generated primary and/or secondary diagnoses for the matches. Additionally or alternatively, the back-end system can include one or more primary and/or secondary symptoms in locating matches.

The method 1100 ends at 1110. In some implementations, the method 1100 may repeat continuously or periodically. The method 1100 may be run in multiple instances in parallel, for example as many threads operating on one or more processors.

Figure 12:
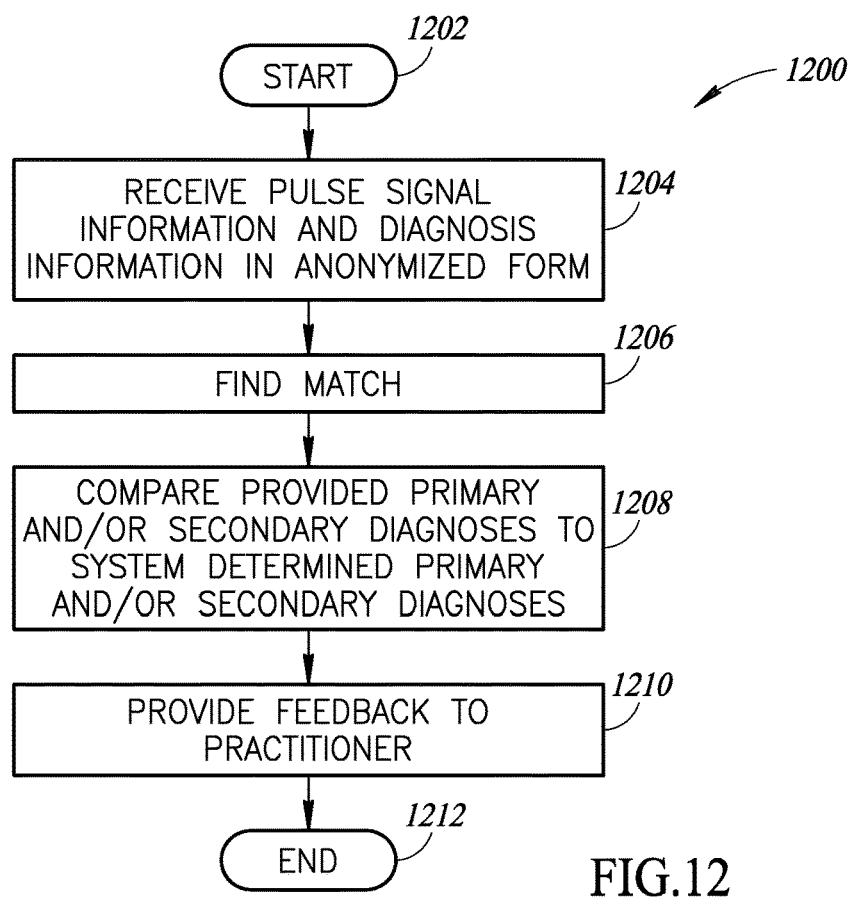
FIG. 12 is a flow diagram of a method of operation in a diagnostic system, for example a runtime system of a back-end system to process diagnostically relevant information for a number of subjects, according to one illustrated implementation.

FIG. 12 shows a method 1200 of operation in a diagnostic environment, according to at least one illustrated embodiment. The method 1200 can be implemented by a back-end system, similar or even identical to that illustrated and described with respect to FIG. 1. For example, the method 1200 can be executed by a runtime system, for example using a machine-learning generated dataset.

The method 1200 starts at 1202. For example, the method 1200 may start on application of power to the back-end system or portion thereof (e.g., runtime system). Alternatively, the method 1200 may start on receipt of an inquiry or request by, or submission of collected information from, a front-end system. As a further alternative the method 1200 may start in response to being invoked by a calling program, routine or subroutine. While described in terms of one subject, the method 1200 may be employed with a large number of subjects, and by a large number of practitioners, which may advantageously improve the reliability of the system to the extent such relies on machine-learning techniques.

At 1204, the back-end system receives pulse signal information and diagnosis information in anonymized form. Thus, the received information cannot be related back to a particular subject from which the received information was discerned, except possibly by a practitioner who submitted the anonymized information. In some implementations, even the practitioner who submitted the anonymized information cannot related the submitted information back to a particular subject.

At 1206, the back-end system finds one or more matches for the anonymized information. For example, the back-end system may employ any of a variety of matching algorithms against a database, dataset or other data structure. Also for example, the back-end system can employ a machine-learning system and/or data set to find one or more matches. The back-end system may look for exact matches. Alternatively or additionally, the back-end system can look for loose matches, that is matches where some subset of a set of constraints are satisfied or where some constraints themselves are loosely satisfied (i.e., value of constraint does not exactly match the target value, but is within some acceptable range of the target value).

At 1208, the back-end system compares one or more primary and/or secondary diagnoses provided by a practitioner to one or more system determined or generated primary and/or secondary diagnoses. Thus, the back-end system can determine whether a practitioner's primary and/or secondary diagnoses match those generated by the system using a database or dataset that is generated from a large population of subjects and practitioners, and hence a large population of pulse waveforms and conditions, ailments or maladies. Additionally or alternatively, the back-end system can determine how closely a practitioner's primary and/or secondary diagnoses matches those generated by the system.

At 1210, the back-end system provides feedback to practitioner. Feedback can take many forms. For example, feedback can include an indication of the practitioner's primary and/or secondary diagnoses and an indication of the system generated primary and/or secondary diagnoses for a given set of diagnostically relevant information. Feedback can include an indication of a most popular or highest occurring primary and/or secondary diagnoses for a given set of diagnostically relevant information. Feedback can include an indication of less popular, yet still common primary and/or secondary diagnoses for the given set of diagnostically relevant information. Feedback can include assigning a score based at least in part on how closely a practitioner's primary and/or secondary diagnoses matches those generated by the system.

The method 1200 ends at 1212. In some implementations, the method 1200 may repeat continuously or periodically. The method 1200 may be run in multiple instances in parallel, for example as many threads operating on one or more processors.

Figure 13:
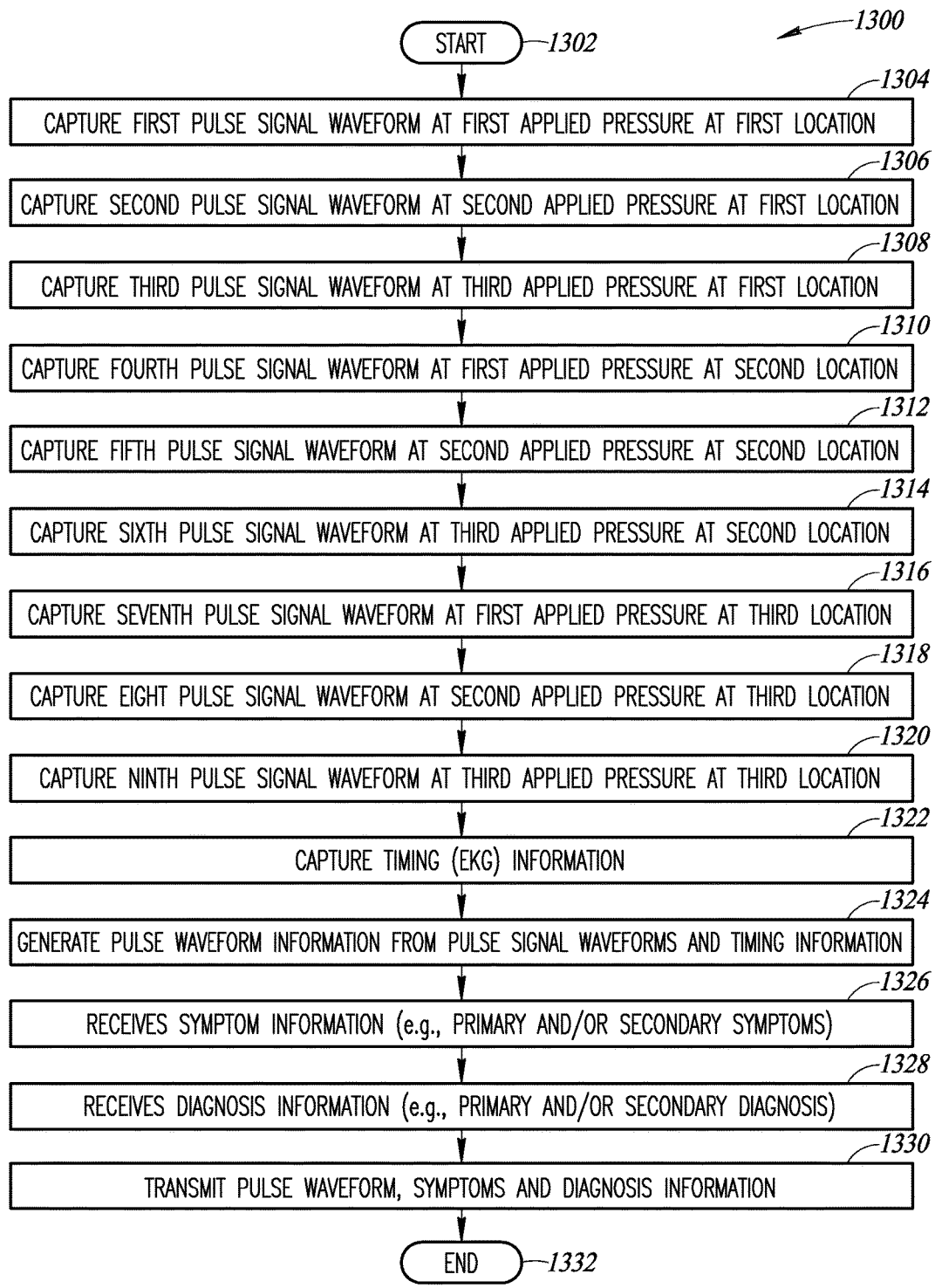
FIG. 13 is a flow diagram of a low level method of operation in a diagnostic system, for example a front-end system to collect diagnostically relevant information for a number of subjects, according to one illustrated implementation.

FIG. 13 shows a method 1300 of operation in a diagnostic environment, according to at least one illustrated embodiment. The method 1300 can be implemented by a front-end system, similar or even identical to that illustrated and described with respect to FIG. 1.

The method 1300 starts at 1302. For example, the method 1300 may start on application of power to the back-end system or portion thereof (e.g., runtime system). Alternatively, the method 1300 may start on receipt of an inquiry or request by, or submission of collected information from, a front-end system. As a further alternative the method 1200 may start in response to being invoked by a calling program, routine or subroutine. While described in terms of one subject, the method 1300 may be employed with a large number of subjects, and by a large number of practitioners, which may advantageously improve the reliability of the system to the extent such relies on machine-learning techniques.

At 1304, one or more sensors or transducers captures a first pulse signal waveform at a first applied pressure at a first location along an artery (e.g., radial artery). At 1306, one or more sensors or transducers capture a second pulse signal waveform at a second applied pressure at a first location along the artery. At 1308, one or more sensors or transducers capture a third pulse signal waveform at a third applied pressure at a first location along the artery.

At 1310, one or more sensors or transducers captures a fourth pulse signal waveform at a first applied pressure at a second location along the artery. At 1312, one or more sensors or transducers capture a fifth pulse signal waveform at a second applied pressure at a second location along the artery. At 1314, one or more sensors or transducers capture a sixth pulse signal waveform at a third applied pressure at a second location along the artery.

At 1316, one or more sensors or transducers capture a seventh pulse signal waveform at a first applied pressure at a third location along the artery. At 1318, one or more sensors or transducers capture an eight pulse signal waveform at a second applied pressure at a third location along the artery. At 1320, one or more sensors or transducers capture a ninth pulse signal waveform at a third applied pressure at a third location along the artery.

The pulse signal waveforms represent pulse waveforms captured through the skin tissue of the subject 106, preferably at one or more locations along a radial artery, proximate a wrist bone on a thumb side of a hand of a subject, and at one or more levels of applied force or pressure. The method is advantageously noninvasive, requiring no needles or puncturing of the skin.

The first, the second, and the third locations are preferably closely spaced from one another, for instance within a width an adult human finger (e.g., $5/8$ inch). The pulse signal waveforms at various locations at a given applied force or pressure are preferably captured temporally proximate in time to one another (e.g., within 2 milliseconds).

At 1322, one or more sensors or transducers capture timing. For example, one or more EKG sensors or electrodes can detect electrical activity of the heart of the subject. Alternatively, an echogram may capture motion of the heart of the subject. The timing information can, for example, include timing of a start of a pulse cycle, timing of an end of a pulse cycle, timing of a length of a pulse cycle, etc.

The timing information represents an event in a cardiac cycle that is sensed separately from the plurality of pulse waveforms. For example, the timing information represents an electrocardiogram (EKG) signal sensed with an EKG transducer, the pulse signal waveforms being delayed with respect to the electrocardiogram (EKG) signal by a known range of time.

At 1324, the front-end system generates pulse waveform information from pulse signal waveforms and timing information.

At 1326, the front-end system or a component thereof (e.g., user interface system) receives symptom information (e.g., primary and/or secondary symptoms). Such can be entered by a practitioner, and may include subject reported or practitioner observed primary and/or secondary symptoms.

At 1328, the front-end system or a component thereof (e.g., user interface system) receives diagnosis information (e.g., primary and/or secondary diagnosis). Such can be entered by a practitioner, and may include practitioner generated primary and/or secondary diagnosis based on examination of the subject. The examination can, for example, include manual examination of the subject's pulse waveform via the practitioner's own finger(s), such as is typically performed as part of an examination by a traditional Chinese medicine practitioner. The collection of primary and/or secondary diagnoses from a set of traditional Chinese medicine practitioners, and particularly from well-regarded traditional Chinese medicine practitioners, can establish a highly reliable database or dataset from which the system can generate system generated diagnoses.

At 1330, the front-end system or a component thereof transmits the pulse waveform information, symptoms information and/or diagnosis information to the back-end system. The front-end system can employ any communication channels or equipment, including encrypted and unencrypted communications. In at least one implementation, back-end system functions can be provided as a software as a service (SaaS) model, using a Web interface or portal to submit queries or requests, and to receive responses including diagnoses.

In some implementations, the user interface device can include an actuator that can create a known waveform in the cardiovascular system. For example, a solenoid, speaker, ultrasound transducer or other actuator can act as a thumper or pinger to put energy into an artery, which can be detected by one or more of the sensors or transducers of the user interface device. For instance, a known waveform can be introduced into a radial artery on an opposite side of the subject from a side on which the sensors or transducers are placed (e.g., actuator on right forearm, proximate the right wrist, sensors or transducers on the left forearm, proximate the left wrist). The front-end or the back-end system can employ the collected pulse waveform information and known waveform in modeling a hemodynamic system, and in predicting or determining various health metrics.

The method 1300 ends at 1332. In some implementations, the method 1300 may repeat continuously or periodically. The method 1300 may be run in multiple instances in parallel, for example as many threads operating on one or more processors.

Figure 14:
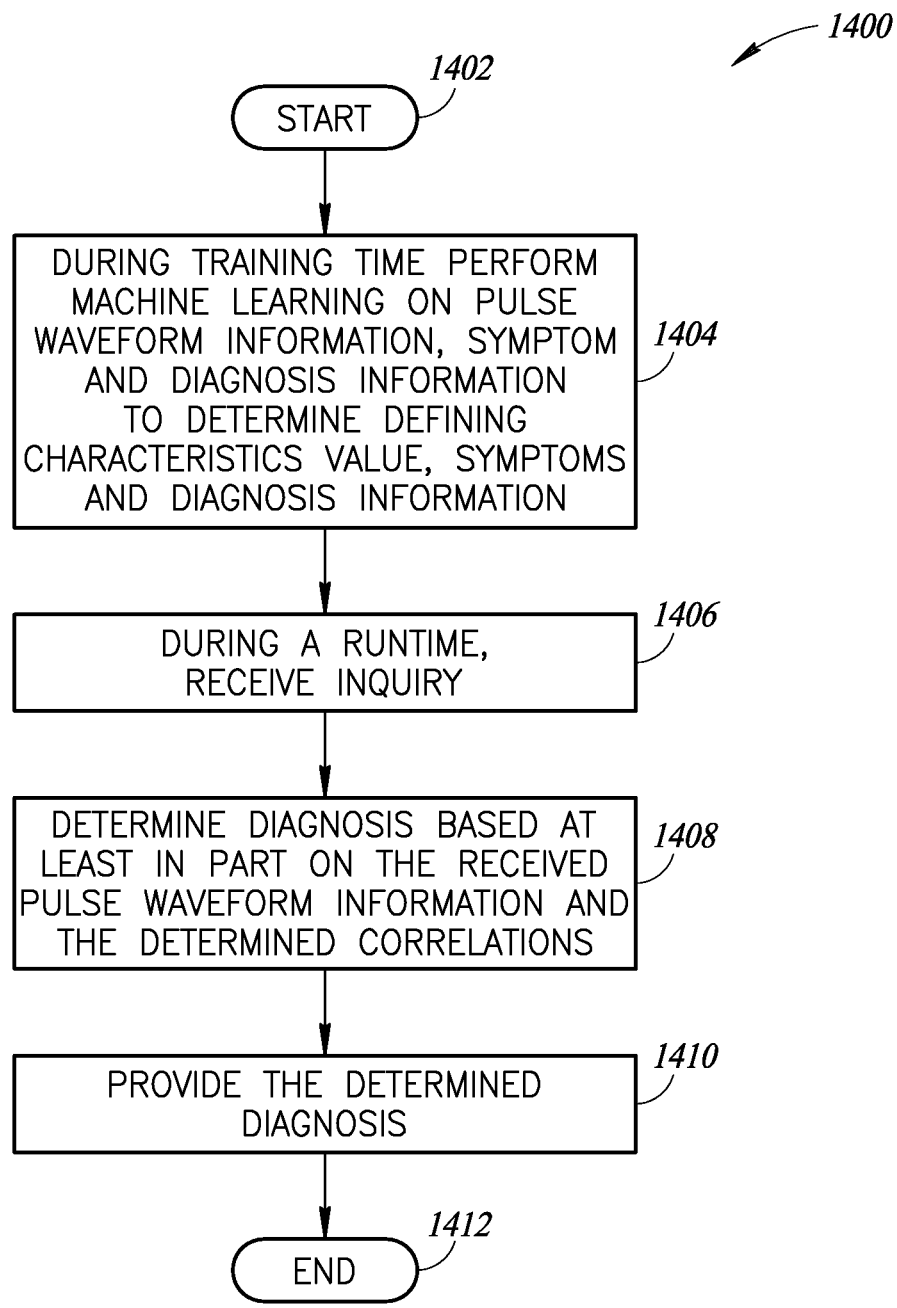
FIG. 14 is a flow diagram of a method of operation in a diagnostic system, for example a runtime system and a training time system both of a back-end system to process diagnostically relevant information for a number of subjects, according to one illustrated implementation.

FIG. 14 shows a method 1400 of operation in a diagnostic environment, according to at least one illustrated embodiment. The method 1400 can be implemented by a back-end system, similar or even identical to that illustrated and described with respect to FIG. 1.

The method 1400 is discussed in terms of a training time portion and a runtime portion. The training time portion can correspond to a training of a model, for example via one or more machine-learning techniques. The training can, for example be implemented via a machine-learning or training system, for instance similar or even identical to that described with respect to FIG. 1. The runtime can correspond to querying the trained model for results, for example by providing diagnostically relevant information and receiving one or more diagnoses based on the diagnostically relevant information, which are preferably generated from a database or dataset that covers a large population of subjects, practitioners, and optionally symptoms, conditions, ailments and maladies.

The method 1400 starts at 1402. For example, the method 1400 may start on application of power to the back-end system or portion thereof. Alternatively, the method 1000 may start on receipt of an inquiry or request by, or submission of collected information from, a front-end system. As a further alternative the method 1400 may start in response to being invoked by a calling program, routine or subroutine. While described in terms of one subject, the method 1400 may be employed with a large number of subjects, and by a large number of practitioners, which may advantageously improve the reliability of the system to the extent such relies on machine-learning techniques.

At 1404, during training time, the machine-learning or training system performs machine-learning on pulse waveform information, symptom and diagnosis information. The machine-learning or training system can, for example, determine a set of defining characteristics or features of various pulse waveforms. The machine-learning or training system can, for example, determine a set of correlations between various values of the defining characteristics or features values and various diagnoses. The machine-learning or training system can, for example, determine a set of correlations between symptoms and the defining characteristics or features or values thereof. The machine-learning or training system can, for example, determine a set of correlations between a) combinations of one or more symptoms and one or more defining characteristics or features or values thereof and b) various diagnoses, for example diagnoses made by traditional Chinese medicine practitioners for similar combinations of one or more symptoms and one or more defining characteristics or features or values thereof.

At 1406, during a runtime, a runtime system receives one or more inquiries or requests, inquiries or requests specifying certain diagnostically relevant information (e.g., pulse waveform representations, for instance including applied force and timing information, symptom information, preliminary diagnoses) for a given subject.

At 1408, during a runtime, the runtime system determines one or more primary and/or secondary diagnoses based at least in part on the received diagnostically relevant information, for instance using the machine-learning dataset (e.g., output layer).

At 1410, during a runtime, the runtime system provides a response to the inquiry or request, which includes the system generated one or more primary and/or secondary diagnoses for the subject. The response can include the initial diagnoses for the particular subject and visit. Alternatively, the response can be confirming or contra to a previously identified diagnosis by the practitioner for the particular subject and visit.

The method 1400 ends at 1412. In some implementations, the method 1400 may repeat continuously or periodically. The method 1400 may be run in multiple instances in parallel, for example as many threads operating on one or more processors.

More Detailed Algorithm

1. Low pass filter the Piezo transducer output(s) with a number N of filter traps. For example, filter below 60 Hz in order to remove hum from the line or mains electrical power. The exact frequency will vary depending on filter slope (i.e., dB/octave).

2. Band pass filter the ECG sensor output(s) with a N number of filter traps, where N is the same number as the number N of low pass filter traps from 1 above so that offset of phase due to the filtering is exactly the same. For example, filter between 10 Hz and 45 Hz. The exact start-stop band frequencies will vary depending on filter slope (i.e., dB/octave). This pulls out just the sharp/fast peak of the main signaling to the heart, which is used as the master timing reference (e.g., timing signal).

3. Window (i.e., trim) the Piezo and ECG arrays to remove filter artifacts at edges (e.g., approximately ½0th the Piezo array).

4. Determine if an end of the Piezo array represents finger movement (e.g., a lifting sensor off artery). Such can be detected, for example, by taking a maximum/peak array sample value in a beginning of a last half third of the Piezo array (N1), and determining if the second last third half of the Piezo array contains a defined multiple (e.g., 2.7 times) greater than a maximum seen in the previous half (N1) of the Piezo array.

5. If the determination at 4 returns a value greater than or equal to the defined multiple (e.g., 2.7 times), then remove a last sixth of both the Piezo array and the ECG array.

6. Determine if a beginning of the Piezo array indicates finger movement (e.g., placing sensor on artery), by taking a maximum/peak array sample value in the beginning of the last half third of the Piezo array (N2), and determining if the first sixth of the piezo array contains a value that is the defined multiple (e.g., 2.7 times) greater than the maximum (N2).

7. If the determination at 6 returns a value that is greater than or equal to the defined multiple (e.g., 2.7 times), then remove the first sixth of both the Piezo array and ECG array.

8. Determine if the Piezo transducer output signal(s) are inverted. For example, take the last third of the Piezo array and check to see if a normalized average of the entire array is above 0.5. For instance, such can be accomplished by normalizing between 0 and 1, summing the elements of the Piezo array, and divide by the total number of array elements.)

9. If the determination at 8 returns a value greater than or equal to 0.5, then invert the Piezo signal.

10. Check to see if Piezo and ECG signal(s) are greater than a minimum signal height for peak detection. If not, the pulse extractor returns zero pulses (i.e., does not process noise from sensors not being connected to patient).

11. Estimate an average of the ECG pulse height for the pulse peak detector, for example by taking the ordered (e.g., smaller values to larger values) array of ECG signals and taking a minimum of the top 5% of the values.

12. Generate an array of ECG pulse locations by searching the ECG array for samples above the a result value of the estimated average from 11, above. Once found, find a maximum value (P1) before the signal falls below the result value again per 11.

13. Take array subsets between ECG pulse locations from the Piezo array to create a two-dimensional (2D) array of all individual Piezo pulses.

14. Index the 2D array of Piezo pulse events in order to look at individual pulses, and compute a pulse propagation time (i.e., time between ECG signaling to time of pulse wave reaching wrist) in milliseconds. Such can be accomplished by finding the index of the maximum value in the Piezo pulse array, and multiplying it by a result of dividing 1000 (i.e. Milliseconds in a second) by a sample rate (in Hz). The result is a one-dimensional (1D) array of the pulse propagation time for every pulse in the recorded data.

15. The pulse interval is the difference in adjacent values in the ECG pulse locations array and multiplying it by the result of dividing 1000 by the sample rate (in Hz).

16. Estimation of patient movement/pulse quality is performed by taking a normalized average of an entire extracted Piezo transducer sensed pulse array (i.e., average pulse), and subtracting the normalized pulse for each pulse in the extracted pulse array. The sum of normalized differences gives a metric that is highly influenced by movement for each pulse in the extracted pulse array.

The system and method can provide a low cost early warning system for cardiovascular and associated diseases, when intervention can be most effective. The systems and methods rely on the acquisition of pulse waveforms that represent the dynamic properties of arterial pulse, which in turn are indicative of the functioning of the cardiovascular system, including the heart, blood, and the blood's interaction and profusion through the blood vessels, tissue and organs. Measurements collected or characteristics identified from measurements include pulse transit time (e.g., reflectometry), blood flow dynamics (e.g., strength of the heart), arterial stiffness (e.g., cardiac efficiency), and blood viscosity. The system can characterize and interpret blood flow dynamics of the cardiovascular system, including a dominant or primary pulse waveform in a current cardiac cycle, and reflections of pulse waveforms from previous cardiac cycles that appear in the current cardiac cycle, although often masked by the dominant pulse waveform of the current cardiac cycle and hence denominated as inferior, secondary or underlying.

The system may be utilized to diagnose a number of conditions, including coronary ischemia, heart valve function, heart muscle inflammation, mitral valve problems, bundle branch blockages, tricuspid valve problems, high blood pressure, aortic valve problems, irregular heartbeat, aortic insufficiency, atrial fibrillation, small vessel blockage, tachycardia, weak heart, bradycardia, enlarged heart, congestive heart, coronary aneurism (hematoma), arterial stiffness, stroke.

The system may generate diagnoses for mammalian patients, especially human patients, based on a spatial and temporal profile of the radial arterial pulse. The patterns of the pulse may be measured by any type of sensor or transducer, not just force or pressure sensitive sensors or transducers. For example, high resolution high frame rate image capture can be employed to detect a pulse as it moves the skin. Acoustic sensors or transducers may likewise sense the pulse through the skin. The system may collect or assemble pulse patterns and matching diagnoses in a database or dataset and employ computer modeling, practitioner input, known diagnoses, known patterns, echocardiograms, mechanical instrumentation or a combination thereof. Other implementations may sense, detect, measure or assess pulse waveforms using light, laser (e.g., with laser source and sensor that detects laser speckle from bodily tissue or skin), magnetic, sensors and/or can employ contrast enhancement techniques.

The pulse pressure, shape, flow, depth, rate, regularity, width, length, smoothness, stiffness, and strength of a patient are measured and the pattern of the pulse is entered into the database or dataset. The system can employ any of a variety of machine learning techniques to draw dependable correlations between diagnosis relevant information and diagnoses. The system can compare a pulse waveform or pattern of a subject to previously entered or cataloged pulse patterns in the database or dataset, and identify corresponding previously entered or cataloged diagnoses, and render a diagnosis and/or suggested remedial action. A machine learning algorithm or technique can, for example, be employed in correlating a diagnoses with blind signal analysis.

An arrangement of sensors or transducers along a blood vessel (e.g., radial artery) can provide the system with a complete description of a three-dimensional undulation of the vessel along an arm, leg, or other area of the body (typically, an arm). The system measures a pressure wave through the area, and correlates the pressure wave versus a timing signal (e.g., pressure wave versus time). The system can further correlate the pressure wave with cardiac events (typically, heart beats). Signal processing is applied to the collected data set and correlations to identify and quantify pressure reflections, timing of reflections, and the amplitude and phase of reflections with respect to primary waves and possibly also with respect to one another.

A data input module can receive pulse waveform data from the sensors or transducers along the blood vessel, and provides the data to a signal processing module. The signal processing module can preprocess the data. For example, the signal processing module can determine a description of the three-dimensional undulation of the vessel. Also for example, the signal processing module can identify the pressure wave versus time. As a further example, the signal processing module can correlate the pressure wave with cardiac events, as described above. The signal processing module can identify and/or quantify pressure reflections, timing of reflections, and the amplitude and phase of reflections with respect to primary waves, and possibly also with respect to one another. The system can then compare all of this information (e.g., pulse waveform information) against stored patterns in a diagnostic database or dataset, looking for a best fit with known pathological "signatures" (e.g., a blocked artery somewhere in the body). The collected data and analysis may be sufficient to identify the pathology very specifically (e.g., blockage, extent of blockage, and location of blockage in the body), or only generally (e.g., a blockage somewhere in the body). An appropriate treatment plan may then be formulated.

A depth of a pulse is a vertical position of an arterial pulse below the measurement surface (e.g., skin), and is rated along a continuum. Rate is the number of beats in a minute. Regularity is the rhythm of the arterial pulse, which is categorized as either regular or irregular. Width is the intensity of the arterial pulse. Length is the range of the arterial pulse that can be sensed. Smoothness is the slickness of the arterial pulse. Stiffness is the elasticity of the radial artery. Strength is the forcefulness of the arterial pulse relative to the change in pressure applied.

As described above, the system assesses a pulse wave form at one or more depths, for example at a superficial, a middle and/or a deep level. A superficial level can be directly below the skin level, and is located by resting sensors or fingers directly above the radial artery, with the only pressure applied being passive weight. The deep level can be situated directly above the surface of the radius. The deep level is located by first occluding the radial artery by exerting significant force or pressure upon the artery, pushing the artery against a surface of a bone (e.g., the radius) until the pulsations cease, and then slowly releasing the force or pressure until the pulsation returns. This type of occlusion causes a subsequent initial rush in the blood flow, rendering it advisable to allow a few seconds for the pulse to equalize, while maintaining the same finger pressure, before pulse assessment continues. The middle level can be located between the superficial and deep levels, for example midway between.

In some implementations, a pulse pattern is measured or characterized by one or more sensors positioned on one or more fingers of a practitioner's finger. In some implementations, sensors are worn on the index, middle and ring fingers, or a combination thereof. In further implementation, multiple sensors may be worn on each finger. In another implementation, sensors may be included in a cuff or sleeve which is put around a limb (e.g., arm) of a subject. Sensors can be arranged in a linear array, or a series of linear arrays (e.g., two-dimensional array) along a finger and/or across a hand.

In some implementations, micro-displacements resulting from a transfer of the pulse undulations under the skin can be measured by an interference of coherent light reflected from the surface of the skin without contact, as viewed by a video camera as laser speckle. Micro-displacements resulting on the surface of the skin may in some cases be measured by processing the signal from a video camera to measure subtle movements of the skin. The sensors or transducers can detect a pulse waveform, as well as an amount of applied force or pressure used to measure the pulse. The sensors or transducers can convert the pulse to a signal that can be transmitted to an analog amplifier. The signal is converted to a digital signal and sent to a transceiver. The received signal is then sent to a digital signal processor. The signal is then sent to a database and compared to other pulse patterns. Once a match is found, the diagnosis for the subject is displayed.

In some implementations, signal analysis on the collected sensor or transducer signals comprises a time series analysis of digital signal streams, including auto-correlation, cross correlations, power spectral distribution, cross spectral distribution, Fourier Analysis, wavelet analysis, principal component analysis, root mean square matching and similar and/or custom analysis tools. These tools can reduce the pulse train into a form of eigenvalues, that enable rapid comparison within large databases of patient data.

Patient data from a database or dataset can be used in various assessments for assessing a health of a subject (e.g., patient). Pulse waveform information can be combined with as little or as much additional patient data as desired. In some implementations, the database or dataset can store patient related data, e.g., a patient identifier and/or patient demographic information. The database can also generate reports using a report generation module. A disease management recommendations module can store various treatment recommendations that can be included in patient reports based on the analysis of the data gathered from the pulse. The comparative data store can store comparative data from healthy patients and/or patients with a chronic illness and combinations of pulse patterns and diagnoses.

In some implementations, a subject may complete a questionnaire to improve the diagnostic capabilities of the system. The questionnaires can address any of a number of health conditions, including current symptoms, past illnesses or maladies. For example, in some embodiments, rating scales may be used to assess the health and mental condition of the subject. According to some implementations, questionnaires can be provided via a Web portal, the user is presented with a Web page or series of Web pages that present the questionnaire to the subject and/or practitioner. The responses may be stored with the patient profile and combined with other patient information or transmitted to the clinician for use when analyzing a diagnosis and determining a course of treatment. Alternatively, responses may be stored anonymously.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one implementation, the present subject matter may be implemented via Application Specific Integrated Circuits (ASICs). However, those skilled in the art will recognize that the implementations disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

Those of skill in the art will recognize that many of the methods or algorithms set out herein may employ additional acts, may omit some acts, and/or may execute acts in a different order than specified.

In addition, those skilled in the art will appreciate that the mechanisms taught herein are capable of being distributed as a program product in a variety of forms, and that an illustrative implementation applies equally regardless of the particular type of signal bearing media used to actually carry out the distribution. Examples of signal bearing media include, but are not limited to, the following: recordable type media such as floppy disks, hard disk drives, CD ROMs, digital tape, and computer memory.

The various implementations described above can be combined to provide further implementations. To the extent that they are not inconsistent with the specific teachings and definitions herein, all of the U.S. patents, U.S. patent application publications, U.S. patent applications, foreign patents, foreign patent applications and non-patent publications referred to in this specification, including U.S. Provisional Patent Application Ser. No. 62/040,990, filed Aug. 22, 2014 is incorporated herein by reference, in its entirety. Aspects of the implementations can be modified, if necessary, to employ systems, circuits and concepts of the various patents, applications and publications to provide yet further implementations.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A diagnostic system, comprising:
at least one processor circuit;
at least one nontransitory memory communicatively coupled the at least one processor circuit and which stores at least one of processor executable instructions or data, execution of which causes the at least processor circuit to:
for each of a number of visits by each of a plurality of subjects, receive respective pulse signal information representative of: i) a first pulse signal waveform captured from the respective subject at a first applied pressure at a first location, ii) at least a second pulse signal waveform captured from the respective subject a second applied pressure at the first location, the second applied pressure different than the first applied pressure, and iii) at least one value indicative of at least one of the first or the second applied pressures, and receive diagnosis information that includes at least a primary diagnosis associated with the respective visit by the respective subject;
for each of the number of visits by each of the plurality of subjects, receive timing information which represents an event in a cardiac cycle that is sensed separately from the plurality of pulse waveforms;
store the received respective pulse signal information, timing information, and diagnosis information to the at least one nontransitory memory; and
perform machine learning on the pulse waveform, the timing information, and diagnosis information during a training time to determine one or more correlations between various ones of a number of defining characteristics of representations of the first and at least the second pulse signal waveforms and the diagnosis information.

2. The diagnostic system of claim 1 wherein for each of the number of visits by each of the plurality of subjects, receives respective pulse signal information representative of: iii) a third pulse signal waveform captured from the respective subject at a third applied pressure at the first location, the third applied pressured different from the first and the second applied pressures.

3. The diagnostic system of claim 2 wherein for a given one of the visits of a given one of the subjects, the received respective pulse signal information further represents a fourth, a fifth and a sixth pulse signal waveform captured from the respective subject at a first, a second and a third applied pressure, respectively, at a second location along a given artery, the second location spaced from the first location.

4. The diagnostic system of claim 3 wherein for a given one of the visits of a given one of the subjects, the first, the second and the third pulse signal waveforms are captured temporally proximate to one another.

5. The diagnostic system of claim 3 wherein for a given one of the visits of a given one of the subjects, the first, the second, the third, the fourth, the fifth and the sixth pulse signal waveforms are captured temporally proximate to one another.

6. The diagnostic system of claim 2 wherein for the given one of the visits of the given one of the subjects, the first, the second and the third pulse signal waveforms represent pulse waveforms captured at a first location along the radial artery proximate a wrist bone on a thumb side of a hand of the subject at the first, the second and the third applied pressures, respectively, and the fourth, the fifth, and the sixth pulse signal waveforms represent pulse waveforms captured at a second location along the radial artery proximate the ulnar, at the first, the second and the third applied pressures, respectively, the second location spaced from the first location.

7. The diagnostic system of claim 6 wherein for a given one of the visits of a given one of the subjects, the received respective pulse signal information further represents a seventh, an eight and a ninth pulse signal waveform captured from the respective subject at a first, a second and a third applied pressure, respectively, at a third location along the radial artery, the third location closely spaced from the first and the second locations.

8. The diagnostic system of claim 7 wherein for a given one of the visits of a given one of the subjects, the first, the second, the third, the fourth, the fifth, the sixth, the seventh, the eight, and the ninth pulse signal waveforms are captured substantially concurrently with one another.

9. The diagnostic system of claim 6 wherein the first, the second and the third pulse signal waveforms each represents respective ones of pulse waveforms captured through a skin of the given subject.

10. The method of claim 1 wherein for at least a subset of the number of visits by at least a subset of the plurality of subjects the received diagnosis information includes at least a secondary diagnosis associated with the respective visit by the respective subject.

11. The diagnostic system of claim 1 wherein for at least a subset of the number of visits by at least a subset of the plurality of subjects, receives at least a primary symptom associated with the respective visit by the respective subject.

12. The diagnostic system of claim 11 wherein for at least a subset of the subset of visits by at least a subset of the subset of subjects, receives at least a secondary symptom associated with the respective visit by the respective subject.

13. The diagnostic system of claim 11 wherein for at least a subset of the number of visits by at least a subset of the plurality of subjects the received diagnosis information includes at least a secondary diagnosis associated with the respective visit by the respective subject.

14. The diagnostic system of claim 1 wherein, during a runtime, the runtime following the training time, for each of a plurality of additional visits, the at least one processor circuit receives pulse waveform information for the respective visit and respective subject, and determines a diagnosis based at least in part on the received pulse waveform information and the determined correlations, and provides the determined diagnosis.

15. The diagnostic system of claim 1 wherein, during a runtime, the runtime following the training time, for each of a plurality of additional visits, the at least one processor circuit receives pulse waveform information and symptom information for the respective visit and respective subject, and determines the diagnosis based at least in part on the received pulse waveform information, the symptom information and the determined correlations, and provides the determined diagnosis.

16. The diagnostic system of claim 1 wherein the timing information represents an electrocardiogram (EKG) signal sensed with an EKG transducer, the pulse signal waveforms being delayed with respect to the electrocardiogram (EKG) signal by a known range of time.

17. The diagnostic system of claim 16 wherein the at least one processor circuit further identifies at least one identifying characteristic in at least one of the pulse signal waveforms based at least in part on the timing information, for each of at least a subset of the number of visits by each of at least a subset of the plurality of subjects.

18. The diagnostic system of claim 1 wherein the received timing information is electrocardiogram timing information which represents an event in a cardiac cycle that is sensed separately from the plurality of pulse waveforms; and the at least one processor circuit further identifies at least one identifying characteristic in at least one of the pulse signal waveforms based at least in part on the timing information, for each of at least a subset of the number of visits by each of at least a subset of the plurality of subjects.

19. A method operation in a diagnostic system that includes at least one processor circuit and at least one nontransitory memory communicatively coupled the at least one processor circuit and which stores at least one of processor executable instructions or data, the method comprising:

for each of a number of visits by each of a plurality of subjects, receiving respective pulse signal information representative of: i) a first pulse signal waveform captured from the respective subject at a first applied pressure at a first location, ii) at least a second pulse signal waveform captured from the respective subject a second applied pressure at the first location, the second applied pressure different than the first applied pressure, and iii) at leave one value indicative of at least one of the first or the second applied pressures, receiving timing information which represents an event in a cardiac cycle that is sensed separately from the plurality of pulse waveforms and receiving diagnosis information that includes at least a primary diagnosis associated with the respective visit by the respective subject;

storing the received respective pulse signal information, timing information and diagnosis information to the at least one nontransitory memory; and determining one or more correlations between various ones of a number of defining characteristics of representations of the first and at least the second pulse signal waveforms and the diagnosis information.

20. The method of claim 19, further comprising: performing machine learning on the pulse waveform and diagnosis information during a training time, by the at least one processor circuit, to determine one or more correlations between various ones of a number of defining characteristics of representations of the first and at least the second pulse signal waveforms and the diagnosis information.

21. The method of claim 20 wherein the timing information represents an electrocardiogram (EKG) signal sensed with an EKG transducer, the pulse signal waveforms being delayed with respect to the electrocardiogram (EKG) signal by a known range of time.

* * * * *